(12) United States Patent
Barbut

(10) Patent No.: US 9,744,337 B2
(45) Date of Patent: Aug. 29, 2017

(54) DEVICES AND METHODS FOR PREVENTING DISTAL EMBOLIZATION USING FLOW REVERSAL AND PERFUSION AUGMENTATION WITHIN THE CEREBRAL VASCULATURE

(75) Inventor: Denise R. Barbut, New York, NY (US)

(73) Assignee: Zoll Circulation, Inc., San Jose, CA (US)

( * ) Notice: Subject to any disclaimer, the term of this patent is extended or adjusted under 35 U.S.C. 154(b) by 1266 days.

(21) Appl. No.: 13/323,112

(22) Filed: Dec. 12, 2011

(65) Prior Publication Data

US 2012/0078287 A1    Mar. 29, 2012

Related U.S. Application Data

(62) Division of application No. 12/639,901, filed on Dec. 16, 2009, now Pat. No. 8,137,374, which is a division of application No. 11/011,948, filed on Dec. 13, 2004, now Pat. No. 7,635,376, which is a division of application No. 09/847,425, filed on May 1, 2001, now Pat. No. 6,830,579.

(51) Int. Cl.
| | |
|---|---|
| A61B 17/08 | (2006.01) |
| A61M 29/00 | (2006.01) |
| A61M 25/10 | (2013.01) |
| A61F 2/01 | (2006.01) |

(52) U.S. Cl.
CPC ........... *A61M 25/104* (2013.01); *A61F 2/013* (2013.01); *A61F 2002/018* (2013.01); *A61F 2230/0006* (2013.01); *A61F 2230/008* (2013.01); *A61F 2230/0065* (2013.01); *A61M 25/1011* (2013.01); *A61M 2025/1015* (2013.01); *A61M 2025/1052* (2013.01)

(58) Field of Classification Search
USPC ........................................................ 606/158
See application file for complete search history.

(56) References Cited

U.S. PATENT DOCUMENTS

| | | | | |
|---|---|---|---|---|
| 4,921,478 | A | * | 5/1990 | Solano et al. ................ 604/509 |
| 6,146,370 | A | * | 11/2000 | Barbut .......................... 604/500 |
| 6,161,547 | A | | 12/2000 | Barbut |
| 6,165,199 | A | | 12/2000 | Barbut |
| 6,217,552 | B1 | | 4/2001 | Barbut et al. |
| 6,231,551 | B1 | * | 5/2001 | Barbut .......................... 604/236 |
| 6,355,010 | B1 | | 3/2002 | Barbut |
| 6,383,172 | B1 | | 5/2002 | Barbut |
| 6,482,172 | B1 | * | 11/2002 | Thramann .................. 604/96.01 |
| 6,530,894 | B1 | | 3/2003 | Barbut |

(Continued)

*Primary Examiner* — Elizabeth Houston
*Assistant Examiner* — L Bachman
(74) *Attorney, Agent, or Firm* — John L. Rogitz

(57) ABSTRACT

Methods of using a medical device having catheter with one or more expandable constricting/occluding members for preventing distal embolization during extracranial or intracranial carotid procedures or vertebral artery procedures by augmenting collateral cerebral circulation by coarctation of the aorta to enhance reversal of blood flow in an internal carotid artery, an external carotid artery, and/or a common carotid artery are disclosed. An interventional catheter can also be advanced into a right cerebral artery and a procedure performed on a lesion in the right cerebral artery.

8 Claims, 44 Drawing Sheets

(56) References Cited

U.S. PATENT DOCUMENTS

| | | |
|---|---|---|
| 6,533,800 B1 | 3/2003 | Barbut |
| 6,555,057 B1 * | 4/2003 | Barbut et al. .................. 422/44 |
| 6,565,552 B1 | 5/2003 | Barbut |
| 6,595,963 B1 | 7/2003 | Barbut |
| 6,595,980 B1 | 7/2003 | Barbut |
| 6,643,415 B1 | 11/2003 | Fukai et al. |
| 6,673,040 B1 * | 1/2004 | Samson et al. .......... 604/101.01 |
| 6,743,196 B2 | 6/2004 | Barbut et al. |
| 6,830,579 B2 | 12/2004 | Barbut |
| 6,848,448 B1 | 2/2005 | St. Germain et al. |
| 6,887,227 B1 | 5/2005 | Barbut |
| 6,942,686 B1 | 9/2005 | Barbut et al. |
| 7,340,298 B1 | 3/2008 | Barbut |
| 7,452,352 B2 | 11/2008 | Barbut |
| 7,635,376 B2 | 12/2009 | Barbut |
| 7,867,195 B2 | 1/2011 | Barbut et al. |
| 7,927,268 B1 | 4/2011 | St. Germain et al. |
| 7,993,324 B2 | 8/2011 | Barbut |
| 8,075,584 B2 | 12/2011 | Barbut |
| 8,137,374 B2 | 3/2012 | Barbut |
| 8,221,383 B2 | 7/2012 | Barbut |
| 2007/0135793 A1 | 6/2007 | Barbut et al. |
| 2007/0239135 A9 | 10/2007 | Barbut |
| 2010/0094330 A1 | 4/2010 | Barbut |
| 2011/0106132 A1 | 5/2011 | Barbut et al. |
| 2012/0089167 A1 | 4/2012 | Barbut |

\* cited by examiner

DEVICES AND METHODS FOR PREVENTING DISTAL EMBOLIZATION USING FLOW REVERSAL AND PERFUSION AUGMENTATION WITHIN THE CEREBRAL VASCULATURE

This is a divisional of U.S. application Ser. No. 12/639, 901, filed Dec. 16, 2009, now U.S. Pat. No. 8,137,374, which is a divisional of U.S. application Ser. No. 11/011, 948, filed Dec. 13, 2004, now U.S. Pat. No. 7,635,376, which is a divisional of U.S. application Ser. No. 09/847, 425, filed May 1, 2001, now U.S. Pat. No. 6,830,579 all of which are expressly incorporated herein by reference in its entirety.

FIELD OF THE INVENTION

The present invention relates generally to devices and methods useful in treating patients with stroke or occlusive cerebrovascular disease. More specifically, the invention provides an extracranial device capable of reversing flow down a vertebral artery, an internal carotid artery, an external carotid artery and/or a common carotid artery, and into the subclavian artery during an invasive procedure, thereby avoiding distal embolization of vascular debris. Various diagnostic or therapeutic instruments, including an angioplasty catheter, stent deployment catheter, atherectomy catheter, and/or a filter, can be introduced through the device for treating the occlusion. The invention may also be useful to reverse flow and pull back embolic debris during a stroke.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. When a patient presents neurological symptoms and signs that resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Outcome following stroke is influenced by a number of factors, the most important being the nature and severity of the resulting neurologic deficit. Overall, less than 80% of patients with stroke survive for at least 1 month, and approximately 35% have been cited for the 10-year survival rates. Of patients who survive the acute period, up to 75% regain independent function, while approximately 15% require institutional care.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are hemispheric ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude the narrow cerebral arteries more distally. The extracranial or intracranial internal carotid artery, commonly affected by atherosclerosis causing symptomatic occlusion in the arterial lumen, is often responsible for hemispheric ischemic stroke and generating thromboembolic material downstream to the distal cerebral vessels. Proposed treatment of the occluded carotid artery in patients with stroke and TIA, or for stroke prevention in patients with asymptomatic flow limiting carotid stenosis, includes angioplasty, stent placement, or atherectomy on the occluded carotid artery. This is also true of the vertebral artery. Unfortunately, placing instrumentation within a diseased artery is associated with increased risk of ischemic stroke, since manipulation of an atheromatous plaque in the arterial wall often causes emboli to dislodge distally in the narrow cerebral arteries.

Current methods of preventing distal embolization from carotid instrumentation include insertion of a blood filter distal to the occlusion and suctioning embolic debris during the procedures. Disadvantages associated with the conventional methods are that (1) inserting a filter through the atheromatous lesion is associated with increased risk of distal embolization, (2) using suction to reverse the flow in the internal carotid artery may increase a patient's blood loss if the suctioned blood is discarded, and (3) systemic anticoagulation and pumping may be required to recycle the suctioned blood back into the arterial or venous system, and such anticoagulation is associated with increased risk of hemorrhage.

New devices and methods are thus needed for patients undergoing carotid procedures for definitive or prophylactic treatment of carotid plaque, which minimize the risk of distal embolization and prevent ischemic stroke.

SUMMARY OF THE INVENTION

The invention provides devices and methods for preventing ischemic stroke in patients undergoing percutaneous invasive vertebral or carotid procedures, including angioplasty, stent placement, atherectomy, and/or filter insertion, by reversing blood flow down a vertebral artery, an extracranial or intracranial internal carotid artery, an external carotid artery, and/or a common carotid artery and into the ipsilateral subclavian artery. In this way, embolic debris generated as a result of placing instrumentation within a diseased artery is diverted to the subclavian artery, thereby preventing stroke by minimizing distal embolization to the narrow cerebral vessels. The devices and methods are also useful to remove an embolus and improve flow (by reversing collateral blood flow across the circle of Willis) in patients with acute stroke.

The invention utilizes devices comprising a catheter having an expandable constricting member at its distal end. The constrictor may be a balloon, in certain cases a toroidal balloon, or a device of any other appropriate shape, so that it can fully or partially occlude blood flow in a blood vessel, e.g., the common carotid artery, the subclavian artery, the brachiocephalic artery, and the aorta. The lumen of the catheter may be adapted for insertion of a therapeutic instrument, such as an angioplasty, atherectomy, and/or stent catheter. A manometer is optionally mounted proximal and/or distal to the constricting member for monitoring blood pressure proximal and/or distal the constrictor. The proximal end of the catheter may include a hemostatic valve.

In another embodiment, the catheter includes a first constrictor/occluder and a second constrictor, each on respective first and second elongate members. The first and second constrictors are collapsed to facilitate insertion into and removal from the vessel, and expanded during use to restrict blood flow. When expanded, the constrictors may have a maximum periphery that conforms to the inner wall of the vessel, thereby providing a sealed contact between the constrictor and the vessel wall. The devices can optionally include a manometer and/or pressure limiter to provide feedback to the variable flow mechanism for precise control of the upstream and downstream blood pressure. In certain embodiments, the constrictor includes a second lumen for passage of other medical devices. Devices such as an infusion, atherectomy, angioplasty, stent placement, or electrophysiologic study (EPS) catheter, can be introduced through the constrictor to insert in the vessel to provide therapeutic intervention at any site rostrally.

In still another embodiment, the catheter includes a second lumen communicating with a proximal end and an infusion port at its distal end. The port is located distal to the distal port of the catheter. The second lumen and its port are adapted for delivering a pharmaceutical agent to the carotid, brachiocephalic and/or subclavian arteries, including an angiographic dye. Any device described in Barbut, U.S. Pat. Nos. 6,146,370 and 6,231,551, both incorporated herein by reference in their entirety, may also be used in the methods described herein.

The invention provides methods for reversing flow in a vertebral or carotid artery having an atheromatous lesion. More specifically, the methods are useful in reversing flow down a vertebral artery, an extracranial or intracranial internal carotid artery, an external carotid artery, and/or a common carotid artery and into the subclavian artery, and optionally into a filter located in the subclavian artery. In a first method of using the devices described above, the distal end of the catheter is inserted into the right brachiocephalic artery. The first catheter can be inserted over a guidewire through an incision on a peripheral artery, including the femoral artery, the subclavian artery, or the brachiocephalic artery. The catheter is positioned to locate the constricting member within the right brachiocephalic artery. Preferably, the constrictor is expanded to completely or partially occlude the right brachiocephalic artery. A second constrictor carried by a second catheter is located in the aorta downstream of the left subclavian artery. The second constricting member is expanded to partially or fully occlude the aorta, thereby augmenting blood flow to the left common carotid artery, the left subclavian artery, and the left vertebral artery.

It will be understood that coarctation in the aorta increases the pressure gradient from the left cerebral arteries to the right cerebral arteries, thereby enhancing flow reversal in the right cerebral arteries (including the right CCA, the right ICA, the right ECA, and the right vertebral artery). At a critically low brachiocephalic pressure downstream or distal to the constriction, blood flow in the carotid and vertebral arteries is reversed to pass over the atheromatous lesion and into the right subclavian artery. The flow reversal can be verified fluoroscopically with dye.

It will be understood that either or both of the aortic constrictor and the brachiocephalic constrictor may be inserted through an incision in the femoral artery. In certain cases, the brachiocephalic constricting catheter is inserted through the catheter that carries the aortic constrictor. Alternatively, the aortic constrictor may be inserted through the femoral artery and the brachiocephalic constrictor may be inserted through the right or left subclavian artery. In a further alternative, both the brachiocephalic constrictor and the aortic constrictor are inserted through the right or left subclavian arteries.

In another method, a coarctation constrictor is positioned in the aorta upstream or downstream of the left subclavian artery, and a second constrictor is positioned in the right subclavian artery upstream of the right vertebral artery. The second constrictor is expanded to reduce pressure distally in the right subclavian artery. The coarctation constrictor is expanded to augment cerebral blood flow to the left subclavian artery, the left CCA, the right brachiocephalic artery, and the right CCA. It will be understood that coarctation in the aorta increases the pressure gadient from the left cerebral arteries to the right vertebral artery, thereby enhancing flow reversal in the right vertebral artery. At a critically low right subclavian pressure downstream or distal to the constriction, blood flow in the vertebral artery is reversed to pass over the atheromatous lesion and into the right subclavian artery. The flow reversal can be verified fluoroscopically with dye. It will be understood that either or both of the aortic constrictor and the subclavian constrictor may be inserted through an incision in the femoral artery. Alternatively, the aortic constrictor may be inserted through the femoral artery and the subclavian constrictor may be inserted through the right subclavian artery. In a further alternative, both the subclavian constrictor and the aortic constrictor are inserted through the right or left subclavian arteries.

In another method, a coarctation constrictor is positioned in the aorta upstream or downstream of the left subclavian artery, and a second constrictor is positioned in the left subclavian artery upstream of the left vertebral artery. The second constrictor is expanded to reduce pressure downstream or distally in the left subclavian artery. The coarctation constrictor is expanded to augment cerebral blood flow to the right subclavian artery, the left CCA, the right brachiocephalic artery, and the right CCA. Coarctation in the aorta increases the pressure gradient from the right cerebral arteries to the left vertebral artery, thereby enhancing flow reversal in the left vertebral artery. At a critically low left subclavian pressure downstream or distal to the constriction, blood flow in the left vertebral artery is reversed to pass over the atheromatous lesion and into the left subclavian artery. The flow reversal can be verified fluoroscopically with dye.

In another method, a coarctation constrictor is positioned in the aorta upstream or downstream of the left subclavian artery, and a second constrictor is positioned in the left common carotid artery. The second constrictor is expanded to reduce pressure downstream or distally in the left common carotid artery. The coarctation constrictor is expanded to augment cerebral blood flow to the left subclavian artery, the right brachiocephalic artery, and the right CCA. It will be understood that coarctation in the aorta increases the pressure gradient from the right cerebral arteries and left vertebral artery to the left CCA, thereby enhancing flow reversal in the left CCA.

In another method, a coarctation constrictor is positioned in the aorta upstream or downstream of the left subclavian artery, and a second constrictor-occluder is positioned in the right common carotid artery or left common carotid artery. Blood flow is reversed down the right internal carotid artery and into the right external carotid artery or down the left internal carotid artery and into the left external carotid artery, when the constrictors are expanded. A filter may be located in the external carotid artery to capture embolic debris. A third constrictor may be located in the external carotid artery to enhance the pressure gradient between the internal carotid artery and external carotid artery to enhance flow reversal in the internal carotid artery.

After blood reversal is confirmed, procedures on either the vertebral artery, the internal carotid artery or branches thereof (e.g., MCA or ACA), external carotid artery, or common carotid artery can be performed by advancing a therapeutic or diagnostic instrument through the lumen and port of the catheter distal to the occluder. An atherectomy catheter, for example, can be introduced to remove the atheroma in the right internal carotid artery without fear of distal embolization.

It will be understood that there are several advantages in using the devices and methods disclosed herein for prevention of distal embolization during use of instrumentation in the carotid arteries. For example, the devices (1) abolish the need for suction distal to the constricting/occluding member, thereby minimizing blood loss, (2) eliminate the need for systemic anticoagulation, pumping, and a second arterial or venous stick, all of which are required where suction is employed, (3) can be used to introduce a variety of diagnostic or therapeutic instruments to the carotid arteries, (4) can be used in any procedures that require instrumentation within the carotid artery, (5) can be used for definitive treatment of acute or subacute ischemic stroke, (6) can be used in the angiogram or fluoroscopy suite available in most hospitals, (7) usually require only one incision site for entry, and (8) can be used to perform an interventional procedure without distal protection (e.g., a distal filter), and without crossing the lesion.

DETAILED DESCRIPTION

The cerebral circulation is regulated in such a way that a constant total cerebral blood flow (CBF) is generally maintained under varying conditions. For example, a reduction in flow to one part of the brain, such as in stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation via the Circle of Willis.

Figure 1:
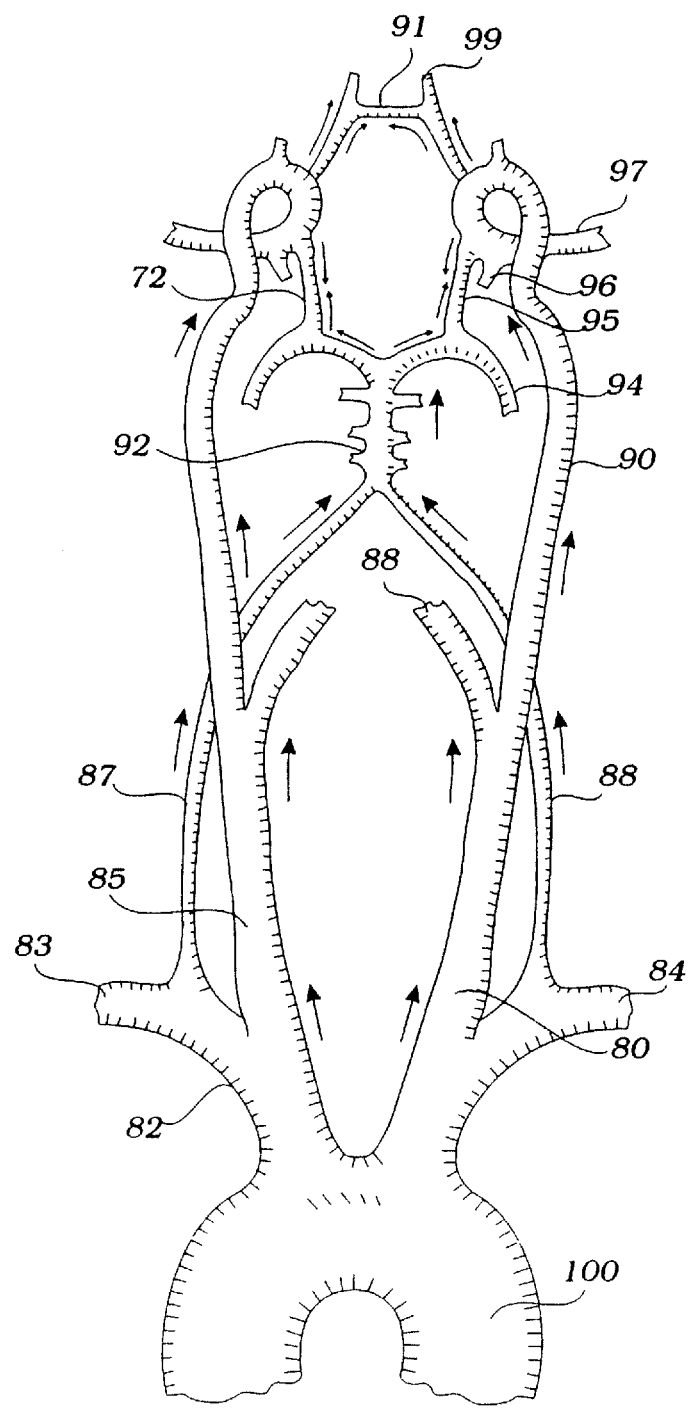
FIG. 1 depicts normal cerebral circulation in the Circle of Willis.

FIG. 1 depicts a normal cerebral circulation and formation of Circle of Willis. Aorta 100 gives rise to right brachiocephalic trunk 82, left common carotid artery (CCA) 80, and left subclavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect respectively with right posterior cerebral artery (PCA) 74 and left PCA 94. The two posterior communicating arteries and PCAs, and the origin of the posterior cerebral from basilar artery 92 complete the circle posteriorly. The left CCA also gives rise to external carotid artery (ECA) 78, which branches extensively to supply most of the structures of the head except the brain and the contents of the orbit. The ECA also helps supply structures in the neck.

Figure 2:
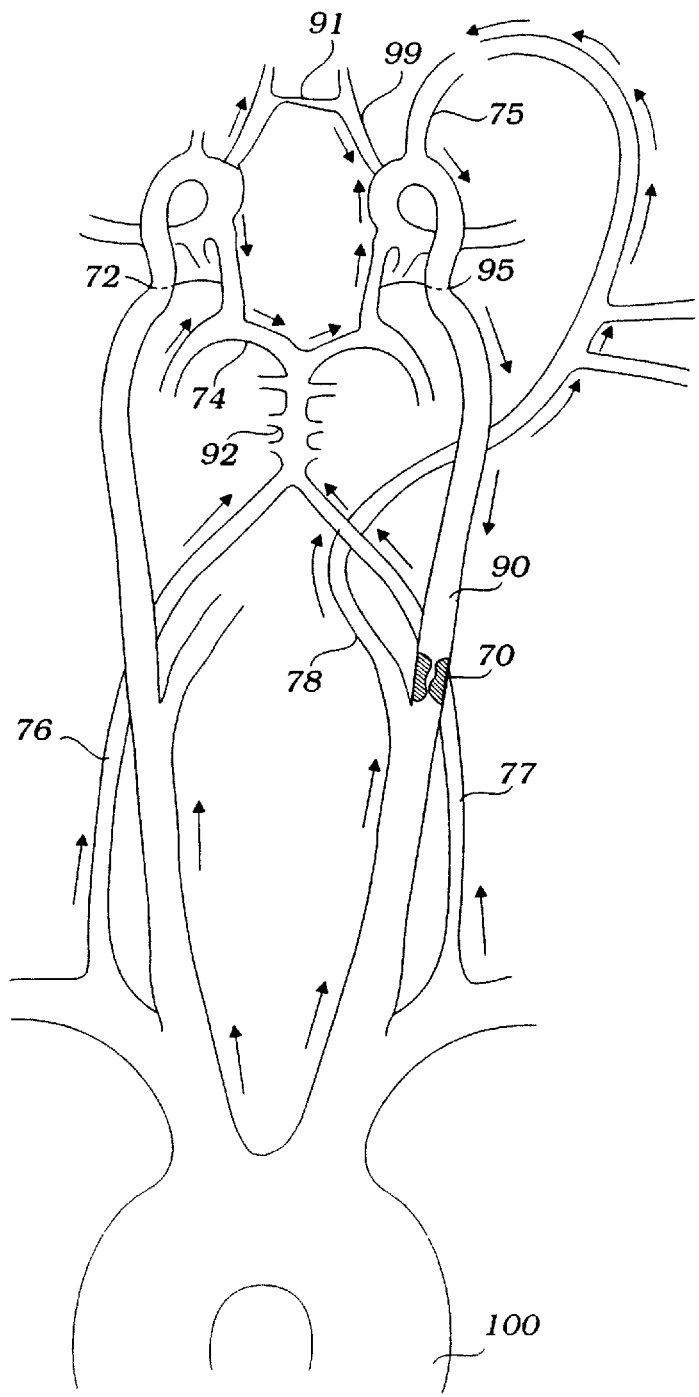
FIG. 2 depicts a reversed circulation in the Circle of Willis to compensate for an occlusion in the left internal carotid artery.

When occluding lesion 70 occurs acutely in left internal carotid artery 90, as depicted in FIG. 2, blood flow in the right cerebral arteries, left external carotid artery 78, right vertebral artery 76, and left vertebral artery 77 increases, resulting in a directional change of flow through the Circle of Willis to compensate for the sudden decrease of blood flow in the left internal carotid artery. Specifically, blood flow reverses in right posterior communicating artery 72, right PCA 74, and left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal to the occluding lesion.

Figure 3:
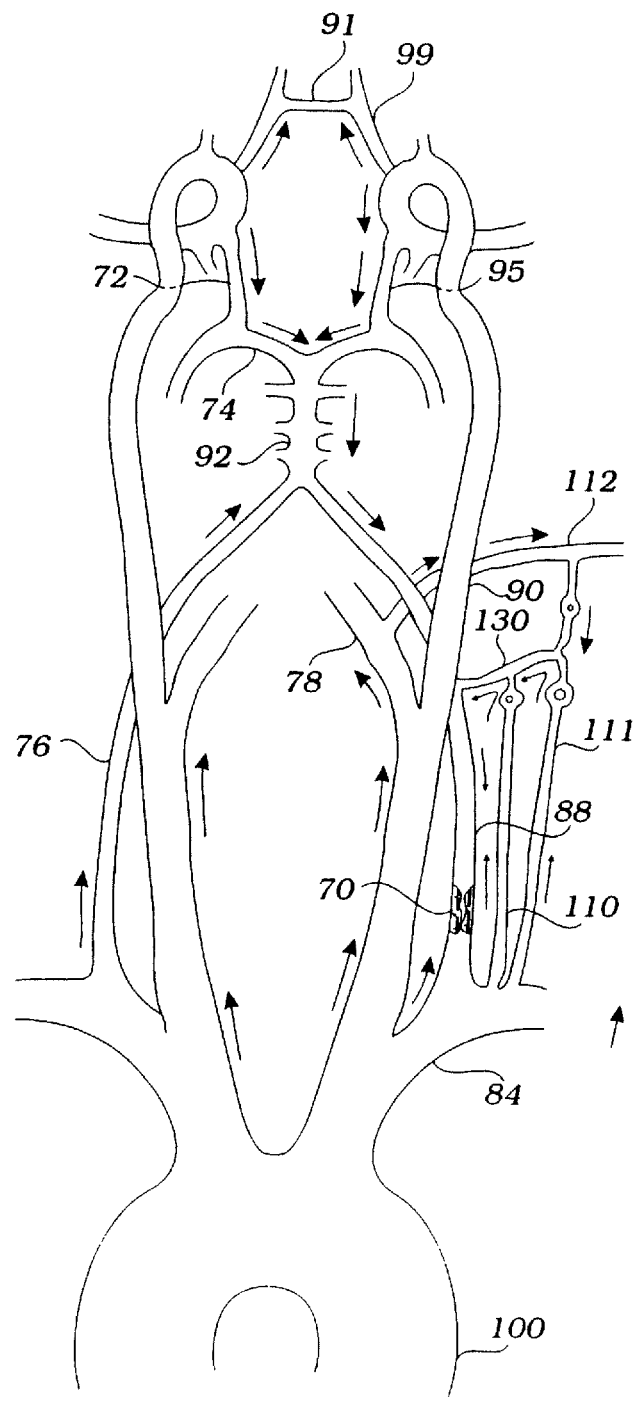
FIG. 3 depicts a reversed circulation in the Circle of Willis to compensate for an occlusion in the left vertebral artery.

When occluding lesion 70 occurs acutely, for example, in left vertebral artery 88, as depicted in FIG. 3, blood flow in the left cerebral arteries, left external carotid artery 78, and right vertebral artery 76 increases, resulting in a directional change of flow through the Circle of Willis down basilar artery 92 to compensate for the sudden decrease of blood flow in the left vertebral artery. Specifically, blood flow reverses in right posterior communicating artery 72, right PCA 74, and left posterior communicating artery 95. Although main collateral blood flow to the left vertebral artery occurs through the right vertebral artery and the Circle of Willis, blood flow may also reverse in communicating branch 130 of left vertebral artery 88 with the left occipital artery, left anterior cervical artery, and left thyrocervical artery. The collateral blood flow through the posterior collateral circulation becomes important when the right vertebral artery is atretic.

When an occlusion occurs in the basilar artery (not shown), blood flow in the right and left cerebral arteries, internal carotid arteries, and external carotid arteries increases, resulting in a directional change of flow through the Circle of Willis down the basilar artery to compensate for the sudden decrease of blood flow. Specifically, blood flow reverses in right and left posterior communicating arteries, and right and left PCA's.

Figure 4A:
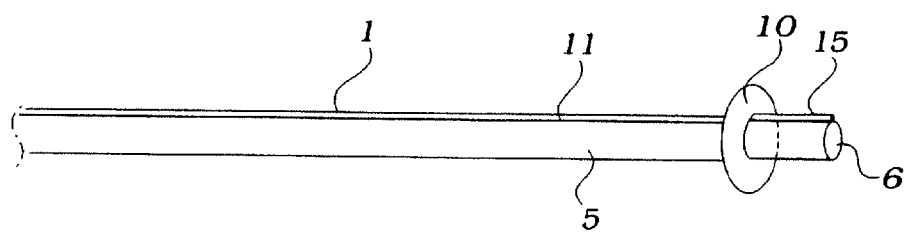
FIG. 4A depicts a distal region of an embodiment of the medical device having an occluding member for prevention of acute stroke during use of instrumentation in a carotid artery.
Figure 4B:
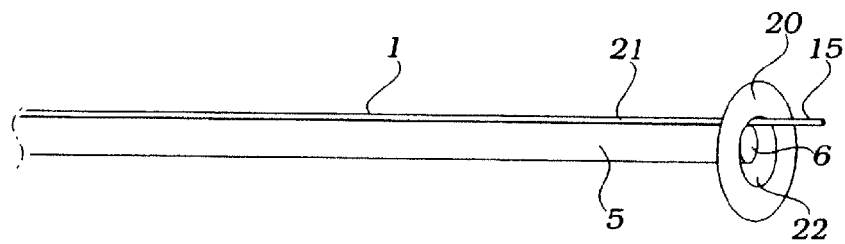
FIG. 4B depicts a distal region of another embodiment of the medical device having a constricting member.

Balloon catheters for achieving flow reversal in carotid arteries were described in Barbut, U.S. Pat. No. 6,146,370, incorporated herein by reference in its entirety. FIG. 4A depicts one embodiment of a device for preventing distal embolization during use of carotid instrumentation. The device comprises catheter 1 and balloon occluder 10. The catheter has lumen 5 communicating with a proximal end and port 6 at a distal end. The lumen and port are adapted for introduction of therapeutic or diagnostic instruments, e.g., an atherectomy catheter, angioplasty catheter, and stent, to a carotid artery. Balloon occluder 10, communicating with inflation lumen 11, is mounted on the distal end of the catheter proximal to port 6. Pressure measuring device 15 is included distal to occluder 10 for monitoring blood pressure downstream of the occluder. The pressure-measuring device can be a manometer or a blood flow channel that communicates with a pressure gauge at a proximal end of the device FIG. 4B depicts another embodiment of the device having constricting member 20 mounted on a distal region of the catheter proximal to port 6. Constricting member 20 communicates with inflation lumen 21. The constrictor has central opening 22 that allows passage of blood. Pressure measuring device 15 is mounted distal to constrictor 20 for monitoring blood pressure downstream the constrictor.

Figure 5A:
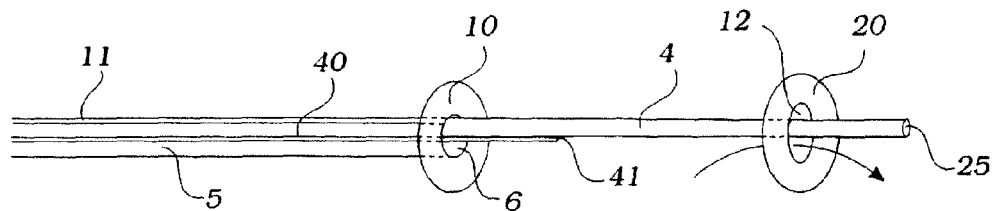
FIG. 5A depicts another embodiment of the device having a proximal occluder and a distal constrictor.
Figure 5B:
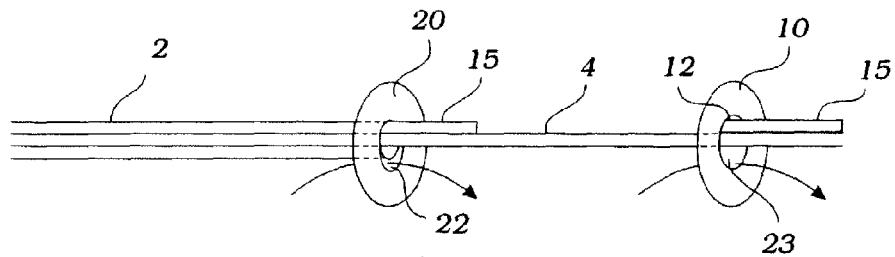
FIG. 5B depicts another embodiment of the device having a proximal constrictor and a distal constrictor.
Figure 5C:
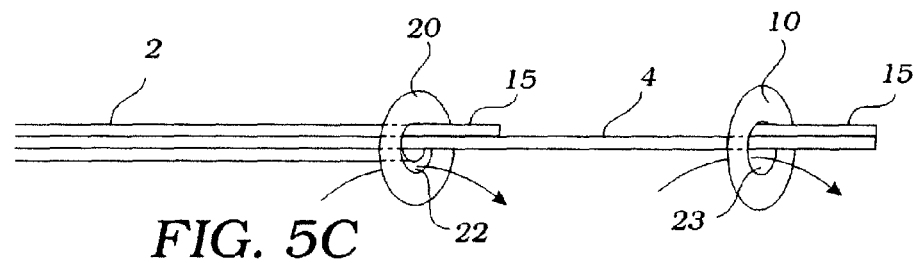
FIG. 5C depicts another embodiment of the device having a proximal constrictor and a distal occluder.
Figure 5D:
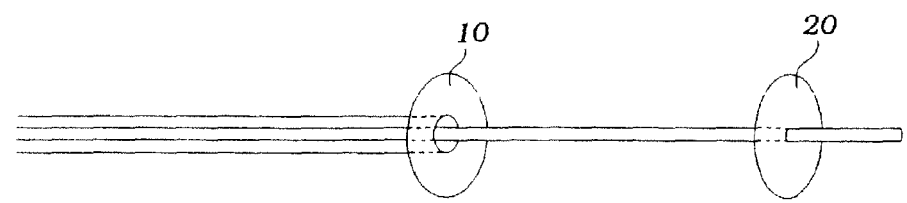
FIG. 5D depicts another embodiment of the device having a proximal occluder and a distal occluder.

FIGS. 5A, 5B, 5C, and 5D depict alternative devices for use in the inventions described herein. Each catheter has first balloon 10 and second balloon 20. All combinations of constrictors and occluders are contemplated. Thus, first balloon 10 may be an occluder, and second balloon 20 may be a constrictor (FIG. 5A). Alternatively, first balloon 10 may be a constrictor, and second balloon 20 may be a constrictor (FIG. 5B). Alternatively, first balloon 10 may be a constrictor, and second balloon 20 may be an occluder (FIG. 5C). Alternatively, first balloon 10 may be an occluder, and second balloon 20 may be an occluder (FIG. 5D). Balloon constrictor 10 is disposed in a distal region of first elongate tubular member 4, and constrictor 20 is disposed in a distal region of second elongate tubular member 2. Each of balloon constrictor 10 and constrictor 20 communicates with a respective inflation lumen (not shown). Constrictor 10 and constrictor 20 have central openings 12 and 22, respectively, that allow passage of blood. Elongate tubular member 4 includes a lumen and port 23 adapted for insertion of therapeutic instruments, e.g., an angioplasty catheter, atherectomy catheter, or stent deployment catheter, into a vessel. Elongate tubular member 4, in certain embodiments, is slideably inserted through elongate tubular member 2, and is moveable longitudinally relative to elongate member 2 and constrictor 10. Manometers 15 are mounted distal to constrictors 10 and 20 for measuring blood pressure downstream the constrictors. Any of the manometers of any device described herein will be understood to include a tube communicating with a pressure gauge at the proximal end of the catheter.

Figure 6A:
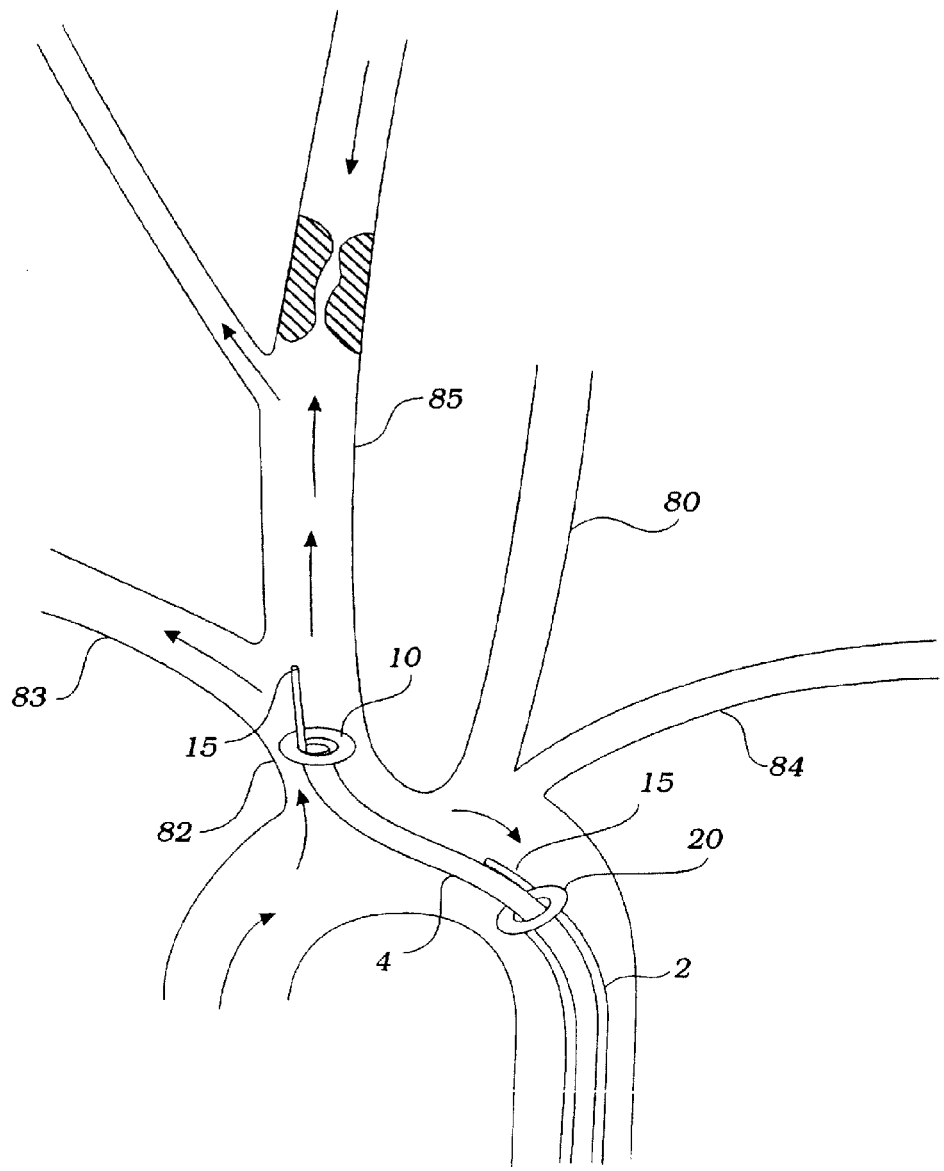
FIG. 6A depicts the device of FIG. 5C inserted in the right brachiocephalic artery through the descending aorta.

In using the device of FIG. 5C to treat an occluding lesion in the right internal carotid artery, for example, a percutaneous incision is first made on a peripheral artery, such as the femoral artery. A guidewire is inserted through the incision into the right brachiocephalic artery in an antegrade direction. The distal end of the catheter is inserted over the guidewire, so that occluder 10 is positioned in right brachiocephalic artery 82 and constrictor 20 is positioned in the descending aorta as shown in FIG. 6A; where needed, a guiding catheter can also be used. Elongate member 4 is slides through elongate member 2 to position constrictor 20 in the descending aorta. The guidewire is then removed from the catheter.

Figure 6B:
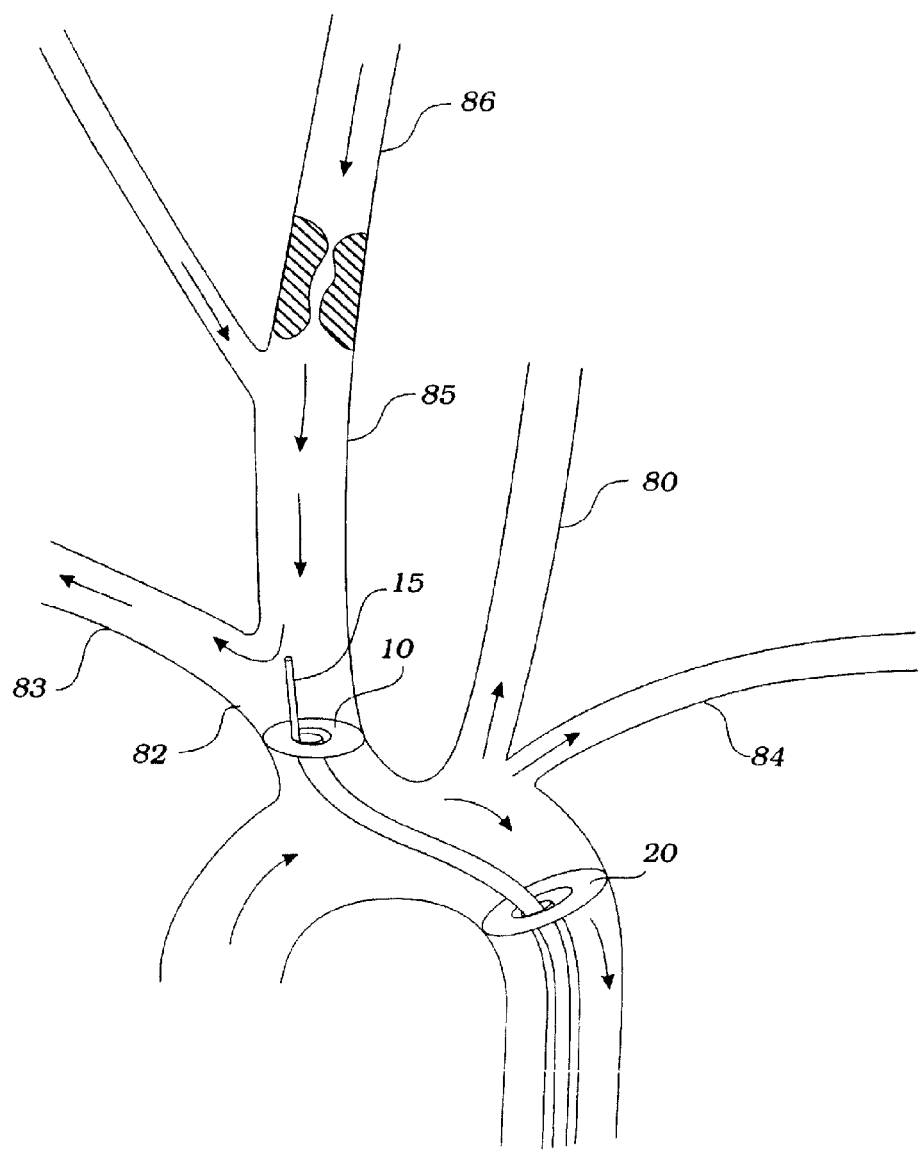
FIG. 6B depicts the expanded occluder in the brachiocephalic artery and expanded constrictor in the descending aorta causing reversal of blood flow from the internal carotid artery to the subclavian artery.

In FIG. 6B, occluder 10 is slowly expanded to constrict right brachiocephalic artery 82 causing progressive decline in right brachiocephalic and right CCA pressure. Constrictor 20 is then slowly expanded to constrict the aorta, thereby causing augmentation of collateral blood flow down right ICA 86 by increasing blood flow to the left CCA and left subclavian artery via the circle of Willis. Alternatively, constrictor 20 is expanded prior to expanding occluder 10. The pressure in right brachiocephalic artery 82 distal to occluder 10 and the pressure in the descending aorta distal to constrictor 20 can be measured by manometers 15. At a critically low pressure in the brachiocephalic artery, blood flow in right ICA 86 and CCA 85 reverses down toward the brachiocephalic artery and into right subclavian artery 83. The reversal of blood flow down the CCA and up the subclavian artery can be verified fluoroscopically with dye.

Figure 6C:
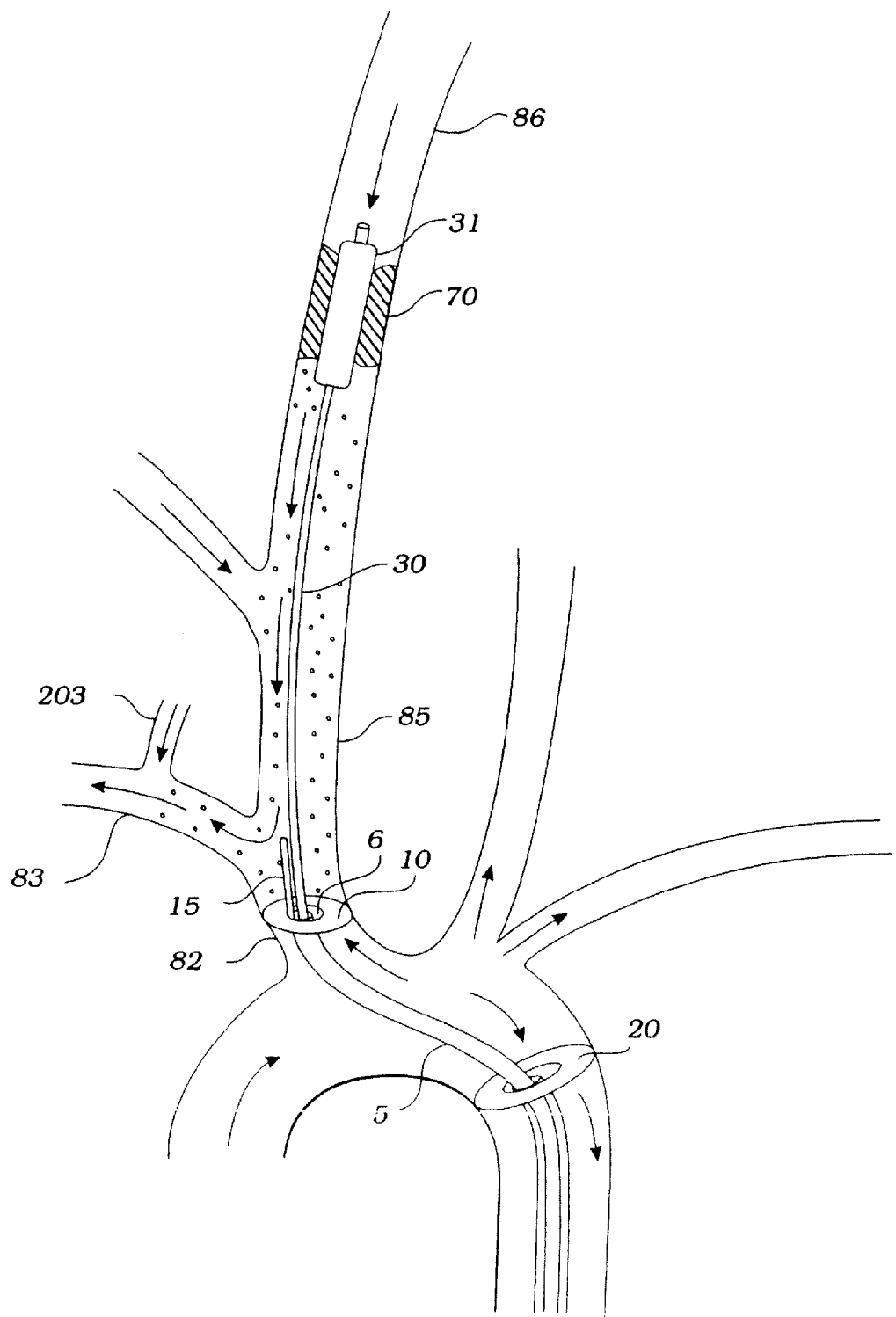
FIG. 6C depicts an angioplasty balloon catheter inserted through the device in FIG. 6B to treat an occluding lesion in the right internal carotid artery.
Figure 6D:
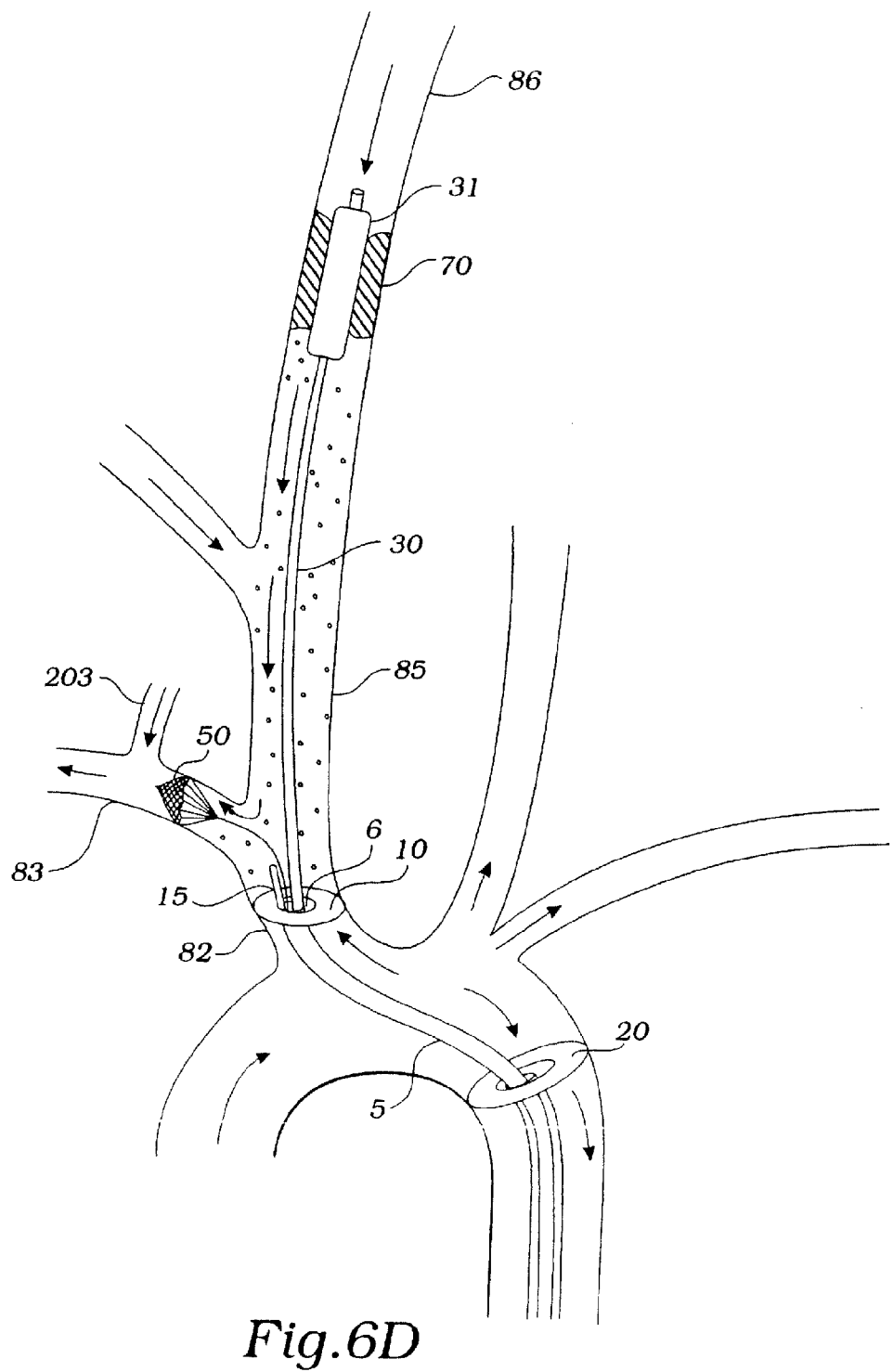
FIG. 6D depicts a filter inserted through the catheter of FIG. 6C in the right subclavian artery to capture embolic debris.
Figure 6E:
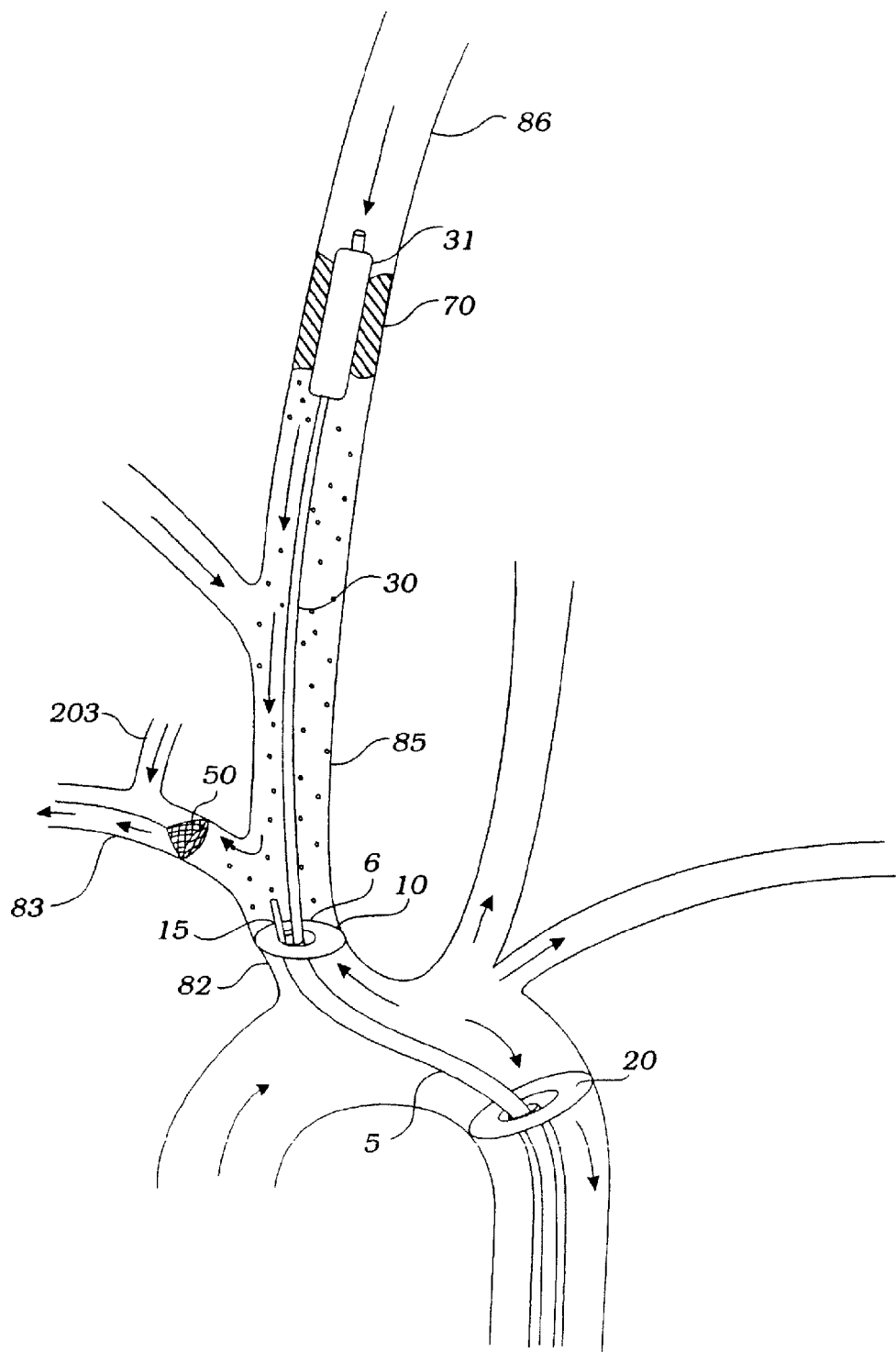
FIG. 6E depicts a filter inserted in the right subclavian artery to capture embolic debris generated by the angioplasty catheter of FIG. 6C.
Figure 6F:
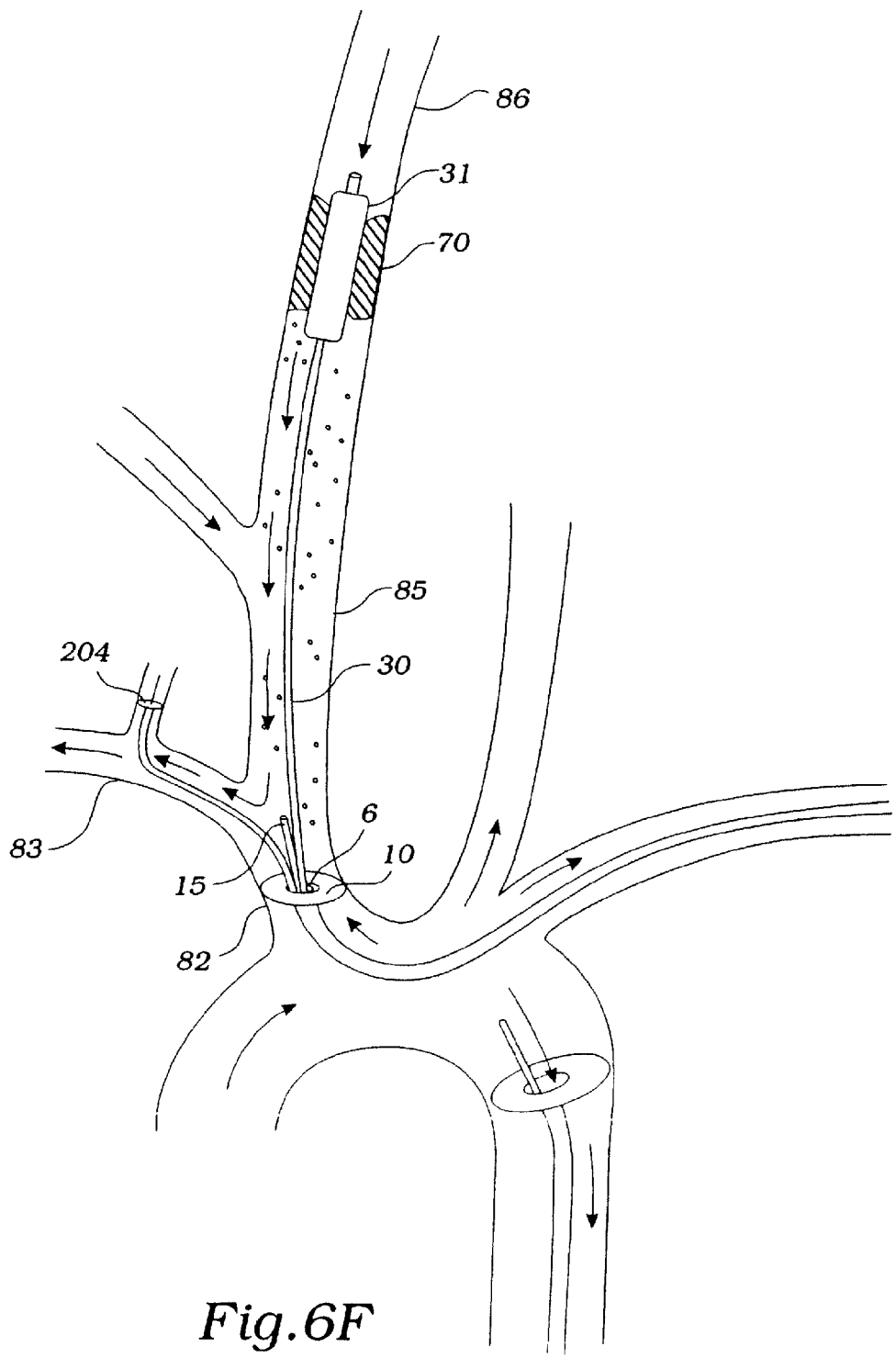
FIG. 6F depicts the use of an occluder to establish carotid flow reversal, a second balloon to protect the vertebral artery against embolization, and a constrictor to achieve aortic coarctation.

After blood reversal is established from the CCA to the subclavian artery, the devices and methods described above can be used in any carotid procedures. For example, in FIG. 6C, interventional catheter 30 carrying angioplasty balloon 31 is introduced through lumen 5 and port 6 of the device. The angioplasty balloon is shown expanding over atheromatous lesion 70 in right ICA 86, thereby compressing the lesion and enlarging the lumenal diameter. Compression of the atheroma by the angioplasty balloon often generates embolic debris, including calcium, atheromatous plaque, and thrombi. With reversal of blood flow from the ICA to the CCA and into the right subclavian artery, distal embolization to the intracranial cerebral arteries is avoided, thereby minimizing risk of ischemic stroke. Distal embolization of the branches of the subclavian artery has far less devastating consequences than the ICA. Blood flow through the affected subclavian artery and its branches is reduced but not abolished due to collateral circulation. For example, collateral flow is established from right vertebral artery 203 into right subclavian artery 83, and this flow reversal in the vertebral artery protects against infarction in the posterior circulation, including the brain stem. In the event that flow reversal does not occur in the vertebral artery upon brachiocephalic occlusion, second balloon 204 (see FIG. 6F) is positioned within the takeoff to the vertebral artery to protect against infarction in the posterior circulation. Filter 50 may be inserted through lumen 5 and deployed in right subclavian artery 83 to capture embolic debris generated during angioplasty as shown in FIG. 6D, thereby preventing embolization to the right arm. Alternatively, filter 50 may be inserted retrograde through right subclavian artery 83, the right radial artery, or the right brachial artery, and deployed in right subclavian artery 83 to capture embolic debris as shown in FIG. 6E.

Figure 6G:
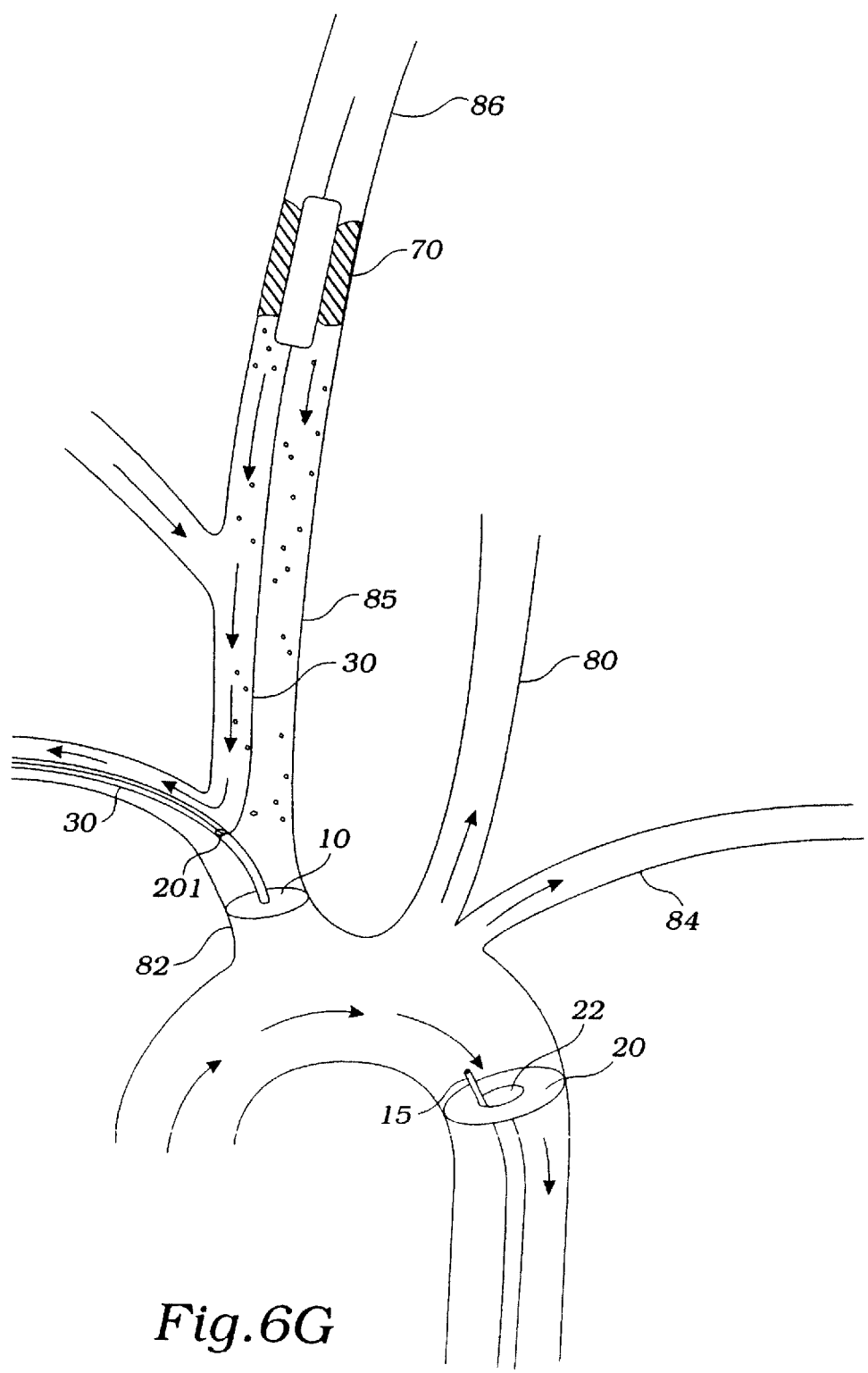
FIG. 6G depicts a constrictor placed in the aorta and an occlusion catheter introduced through the right subclavian artery to treat an atheromatous lesion in the right internal carotid artery.
Figure 6H:
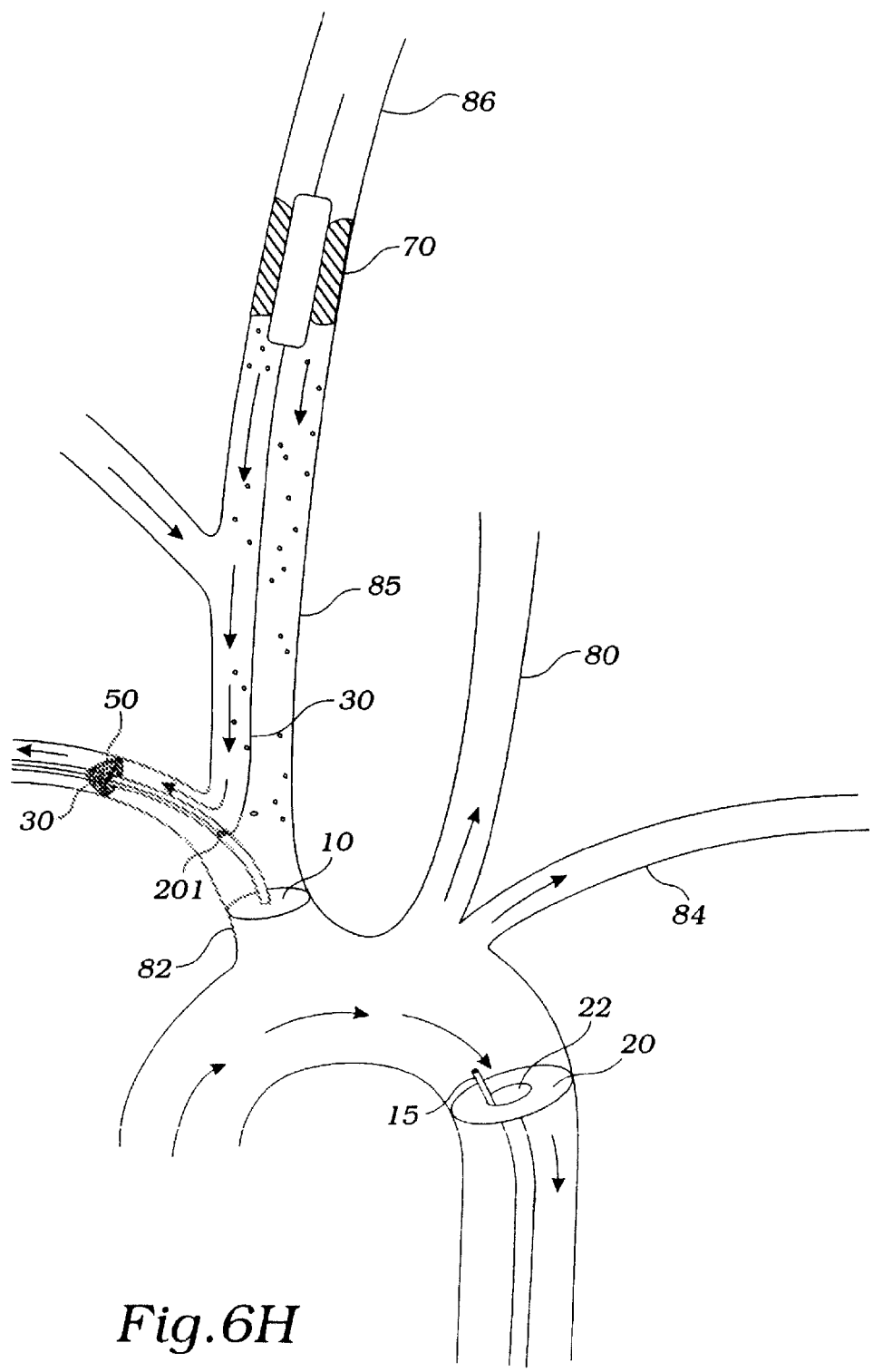
FIG. 6H depicts a filter mounted on the catheter of FIG. 6G to capture embolic debris in the right subclavian artery.

Alternatively, treatment of a right ICA lesion using angioplasty and flow reversal down the right ICA into the right subclavian artery can be achieved by using a catheter adapted for retrograde insertion into the right subclavian artery as shown in FIG. 6G. Aortic coarctation to augment blood flow to the contralateral circulation is achieved by placing the device of FIG. 4B in the descending aorta through a femoral artery. Occlusion member 10 is expanded in the right brachiocephalic artery to establish flow reversal from the right CCA to the right subclavian. Catheter 30, here an angioplasty catheter, is advanced through port 201 to access stenosis 70 in right ICA 86. Filter 50 may be alternatively mounted on the catheter of FIG. 6G and expanded to capture embolic debris as shown in FIG. 6H, thereby preventing emboli from traveling downstream to occlude the arteries of the right arm.

Figure 7A:
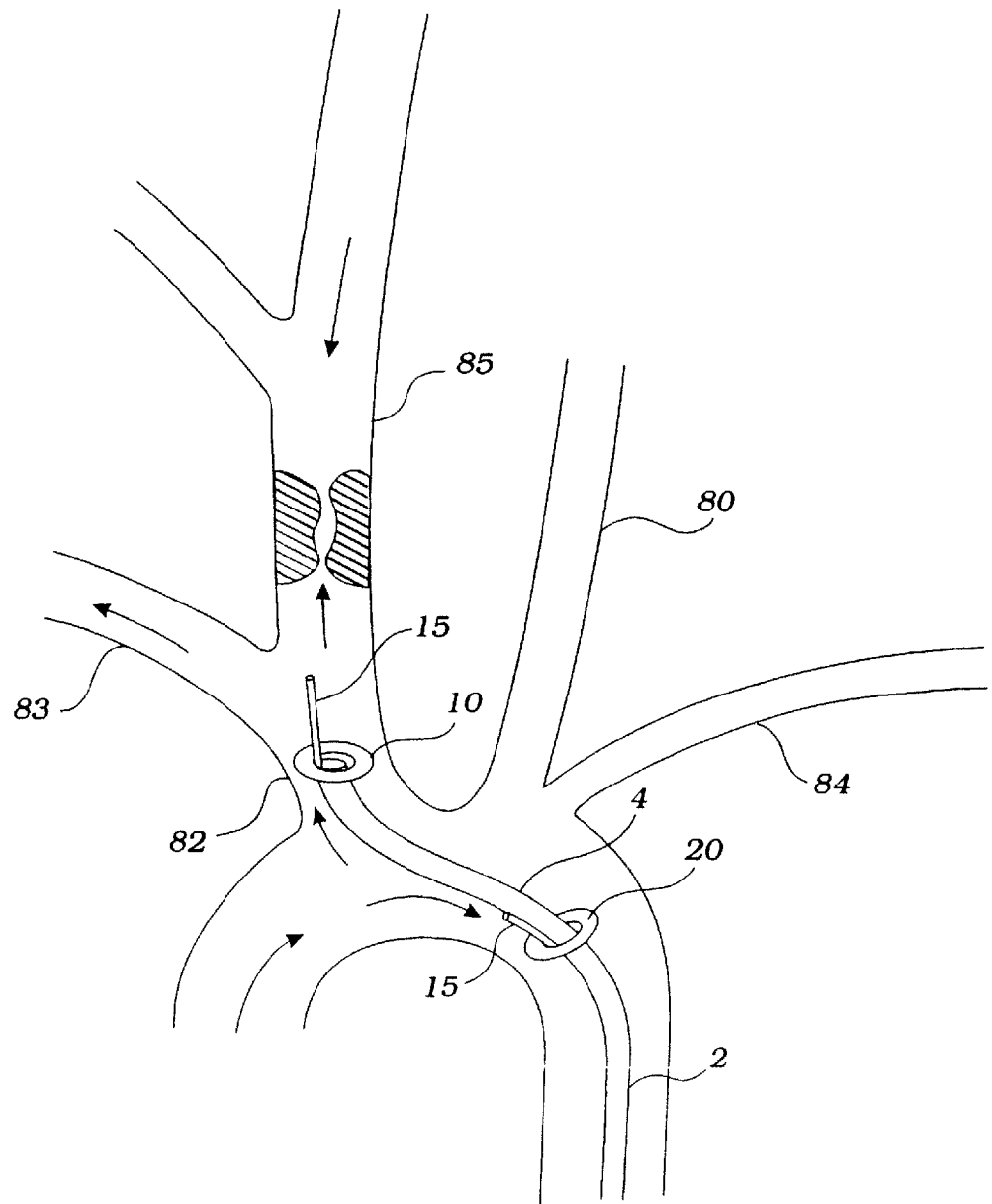
FIG. 7A depicts the device of FIG. 5B inserted in the right brachiocephalic artery.
Figure 7B:
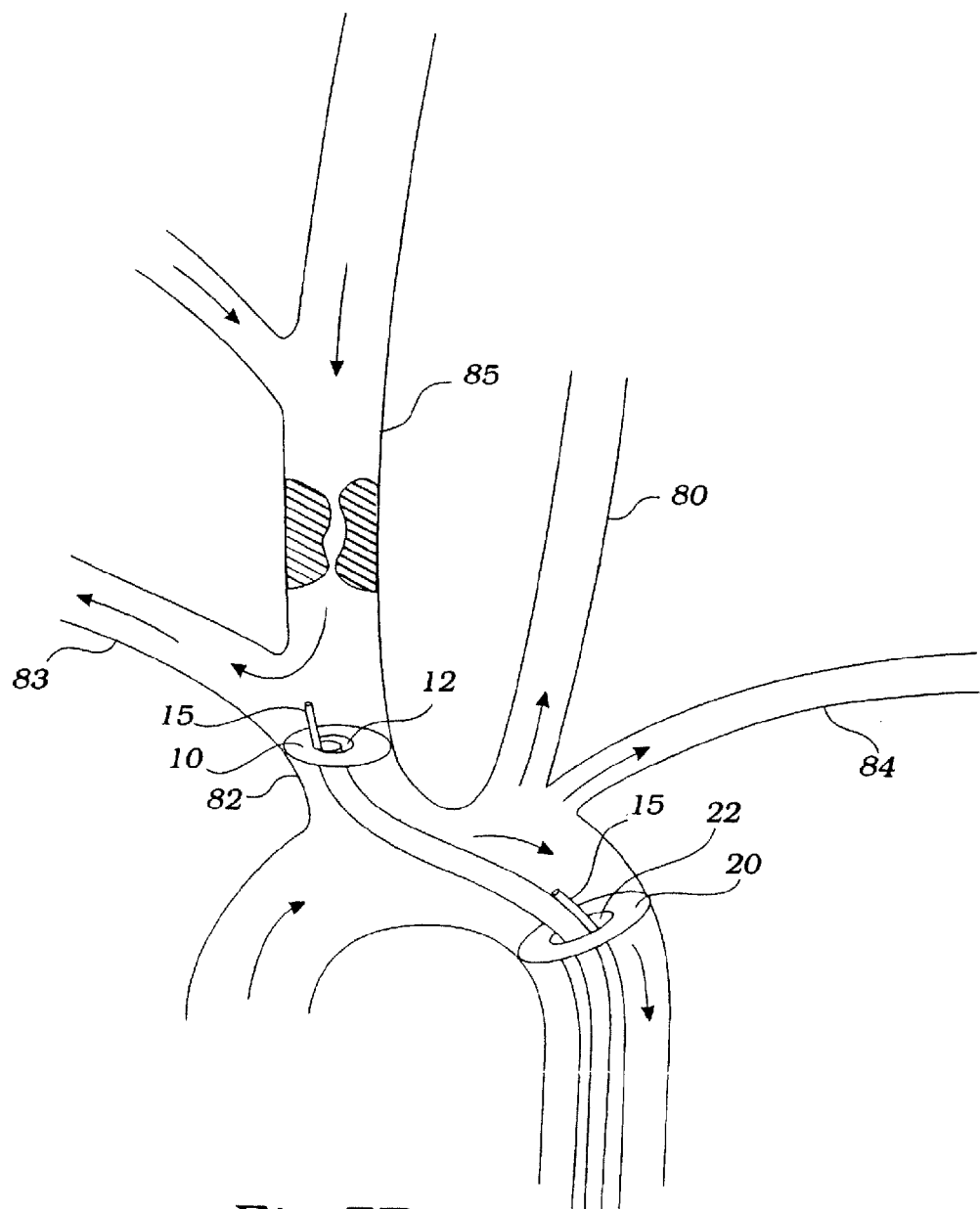
FIG. 7B depicts the expanded constricting members in the right brachiocephalic artery and the aorta causing reversal of blood flow from the common carotid artery to the subclavian artery.
Figure 7C:
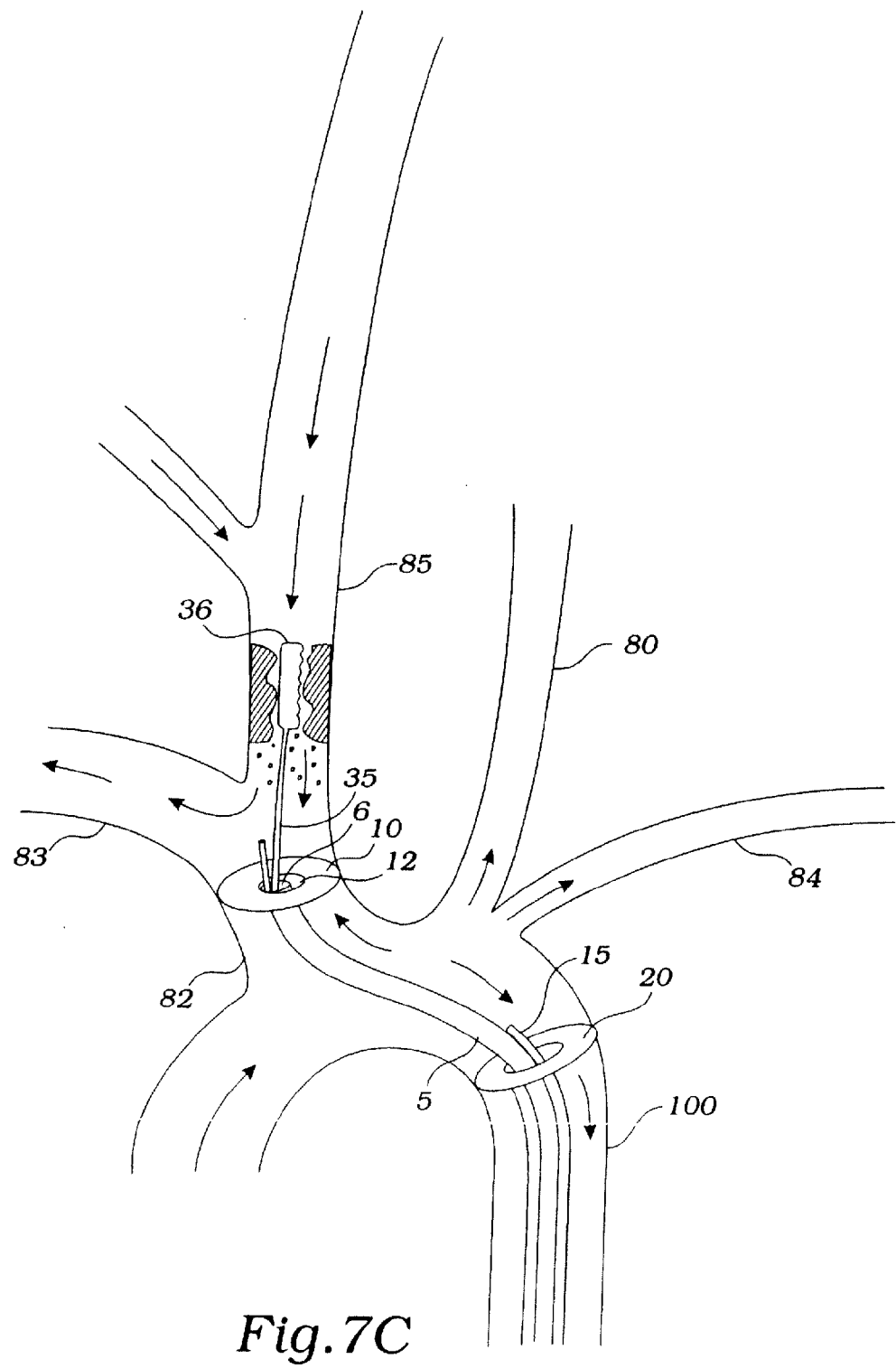
FIG. 7C depicts an atherectomy catheter inserted through the device in FIG. 7B to treat an occluding lesion in the right common carotid artery.

In using the device of FIG. 5B to treat an occluding lesion in the right common carotid artery, for example, the distal end of the device is first inserted into right brachiocephalic artery 82 as shown in FIG. 7A. Constricting member 20 is positioned in the descending aorta by sliding elongate member 4 through elongate member 2. Constricting member 10 is then expanded to constrict the lumen of the brachiocephalic artery, causing reversal of blood flow from right CCA 85 toward brachiocephalic artery 82 and into right subclavian artery 83 as shown in FIG. 7B. Constrictor 20 is also expanded to increase blood flow to left CCA 80 and left subclavian artery 84, thereby causing augmentation of collateral circulation down right common carotid artery 85. Alternatively, constrictor 20 is expanded in the aorta prior to expanding constrictor 10 in the right brachiocephalic artery. After reversal of blood flow is verified angiographically, a therapeutic instrument, such as an atherectomy catheter as depicted in FIG. 7C, is inserted through lumen 5 and port 6 to treat the occluding lesion. Embolic debris generated during the procedure is diverted from CCA 85 toward subclavian artery 83, thereby preventing distal cerebral embolization and ischemic stroke.

Figure 7D:
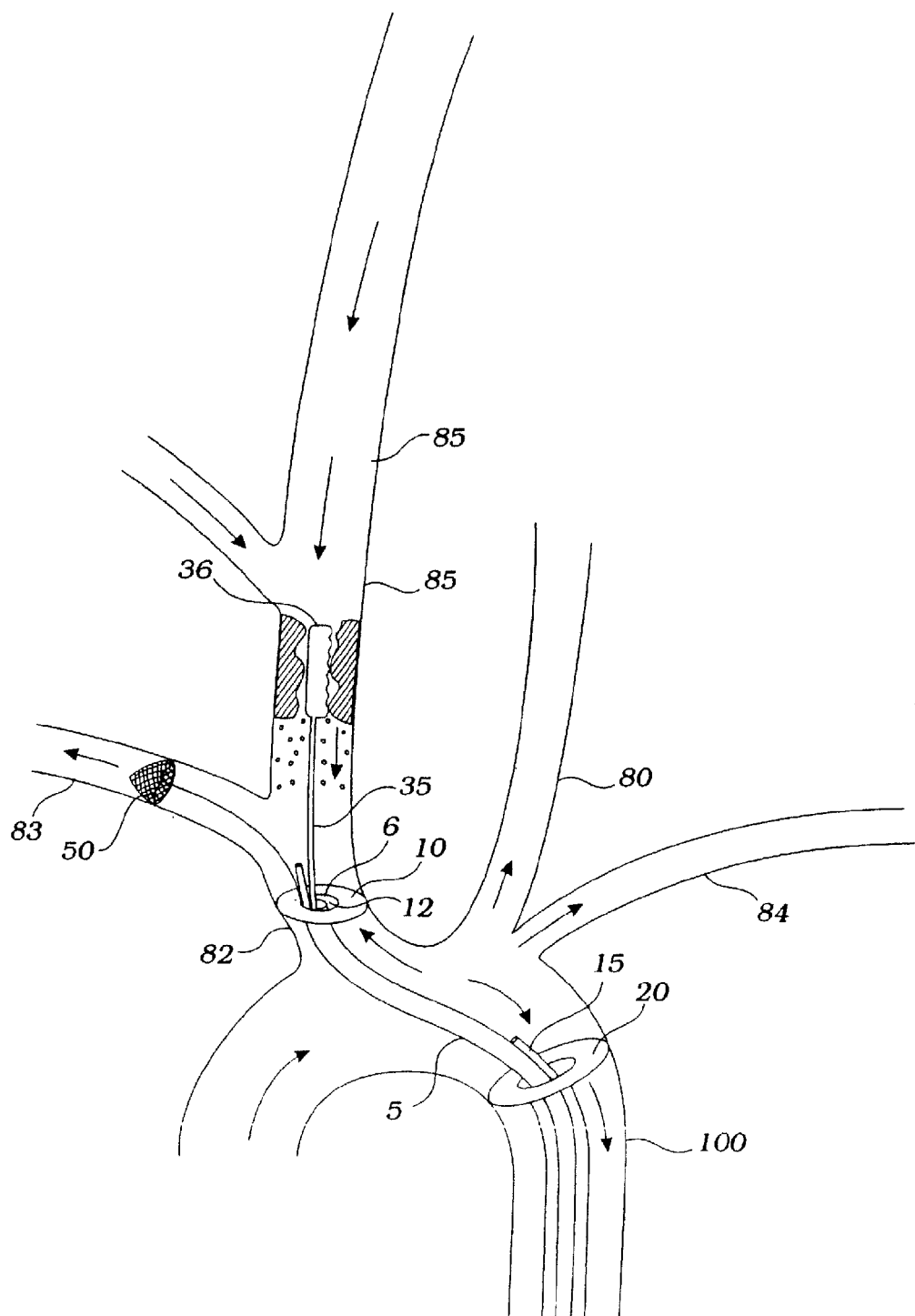
FIG. 7D depicts a filter inserted through the catheter of FIG. 7C and deployed in the right subclavian artery to capture embolic debris.
Figure 7E:
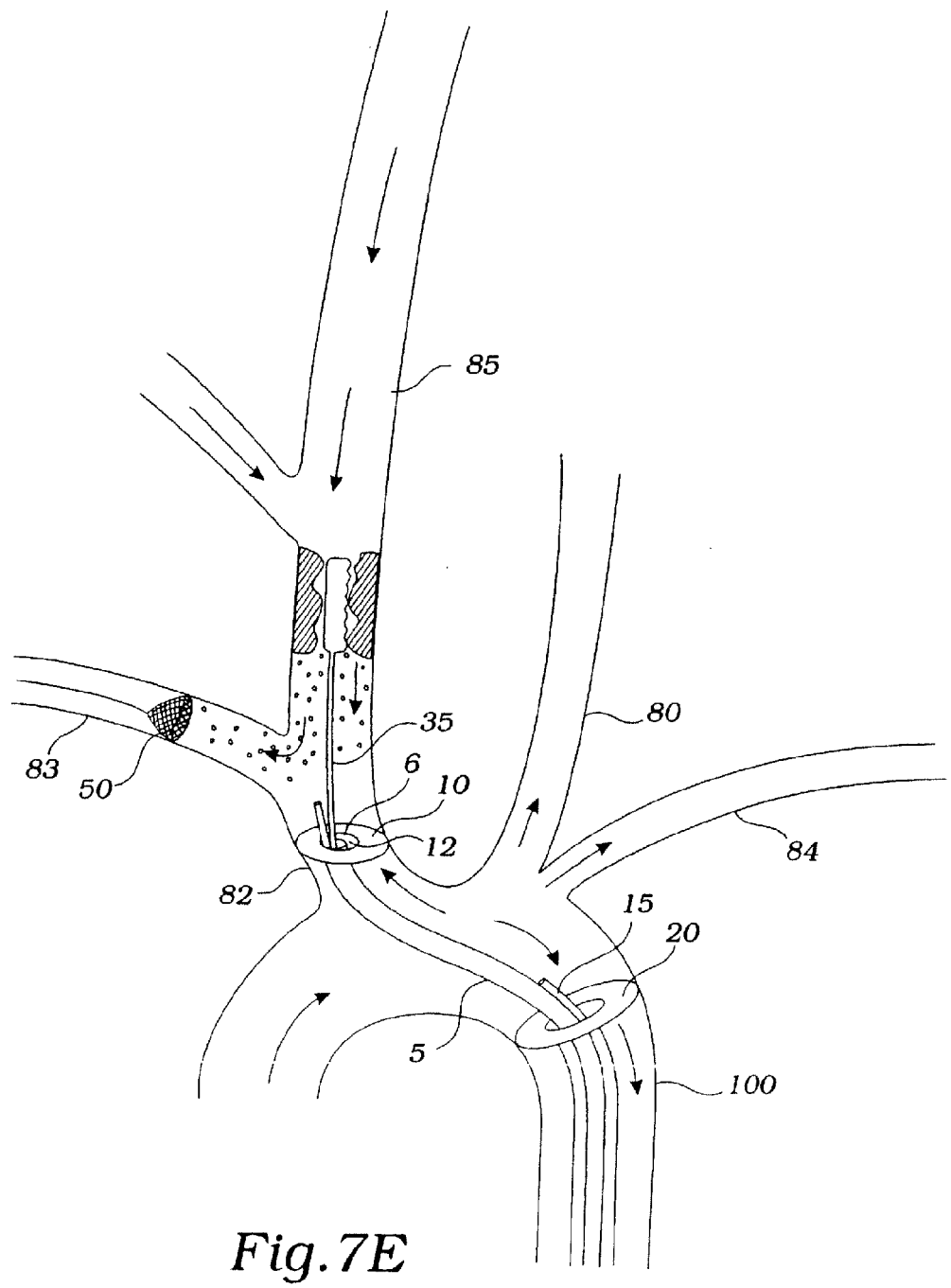
FIG. 7E depicts the method shown in FIG. 7C with a filter inserted in the right subclavian artery in a retrograde direction.

In FIG. 7D, expandable filter 50 may be inserted through lumen 5 of the catheter of FIG. 7C and deployed in right subclavian artery 83 to prevent embolic debris generated during the angioplasty procedure from traveling downstream to occlude the arteries of the right arm. Alternatively, filter 50 may be inserted in right subclavian artery 83 in a retrograde direction from the radial artery, the brachial artery, or the right subclavian artery as shown in FIG. 7E.

The construction of atherectomy catheters is well known in the art and will not be repeated in detail here. The reader is referred instead to Fischell, U.S. Pat. No. 5,409,454; Fischell, U.S. Pat. No. 4,898,575; Rydell, U.S. Pat. No. 4,857,045; Yock, U.S. Pat. Nos. 4,794,931, 5,000,185, and 5,313,949; Jang et al., U.S. Pat. No. 5,507,292; Farr, U.S. Pat. Nos. 4,950,277, 4,986,807, 5,019,088; Shiber, U.S. Pat. Nos. 4,894,051, 4,957,482, 4,979,939, 5,007,896, 5,024,651, 5,135,531; Summers, U.S. Pat. No. 5,087,265; Plassche et al., U.S. Pat. No. 5,318,576; Belknap, U.S. Pat. No. 5,366,464; Jang et al., U.S. Pat. No. 5,402,790; Mazur et al., *Catherization and Cardiovascular Diagnosis* 31:79-84 (1994); Fischell et al., U.S. Pat. Nos. 4,886,061, 5,100,425; and Barbut et al., U.S. Pat. No. 5,662,671, all of which are incorporated herein by reference in their entirety as if fully set forth herein. In other embodiments, catheter 35 may carry angioplasty balloon 36 or a stent.

Figure 8:
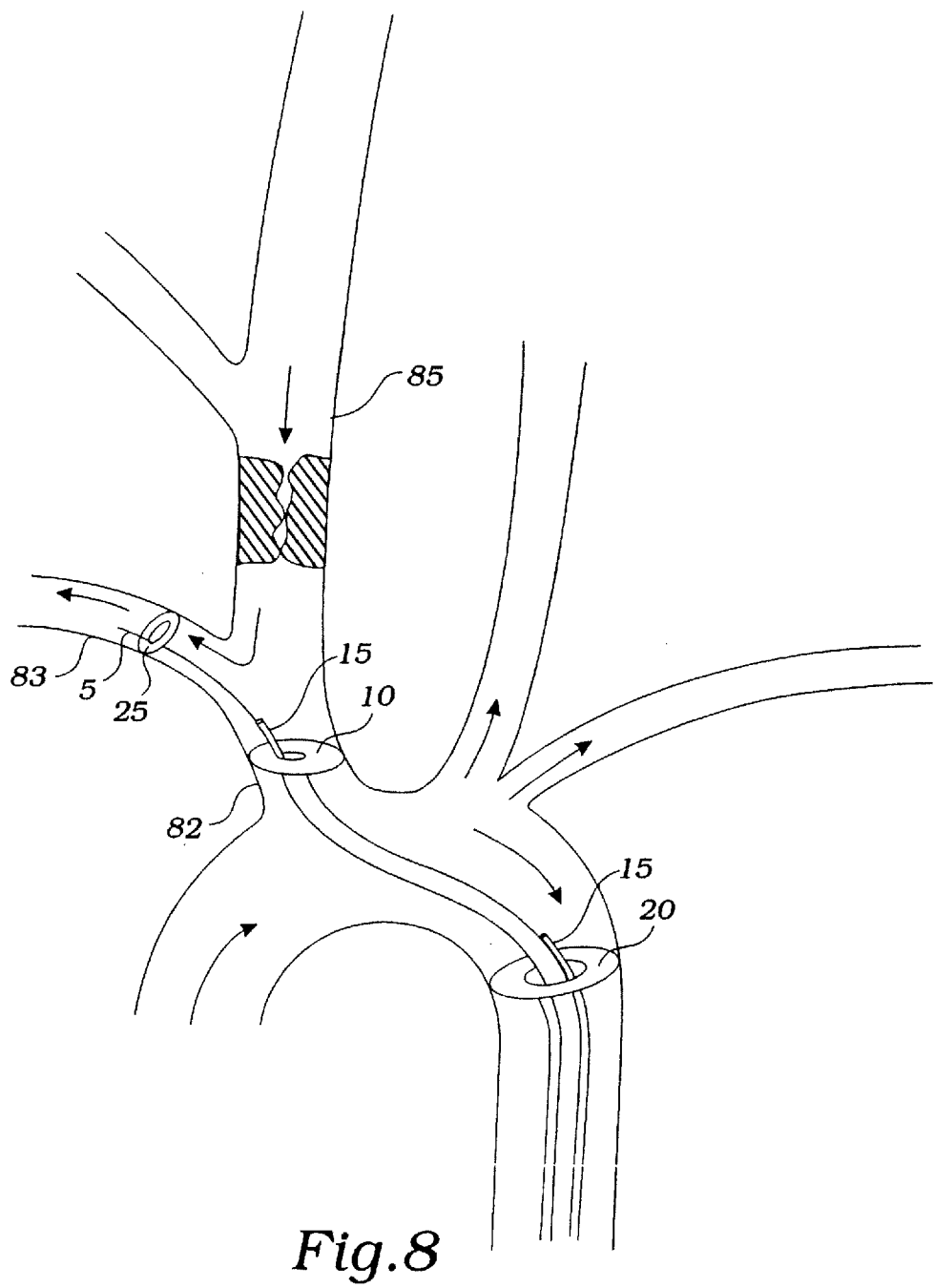
FIG. 8 depicts an alternative embodiment of the device inserted in the right brachiocephalic artery and the right subclavian artery to further increase the pressure gradient between the right common carotid artery and the right subclavian artery.
Figure 8A:
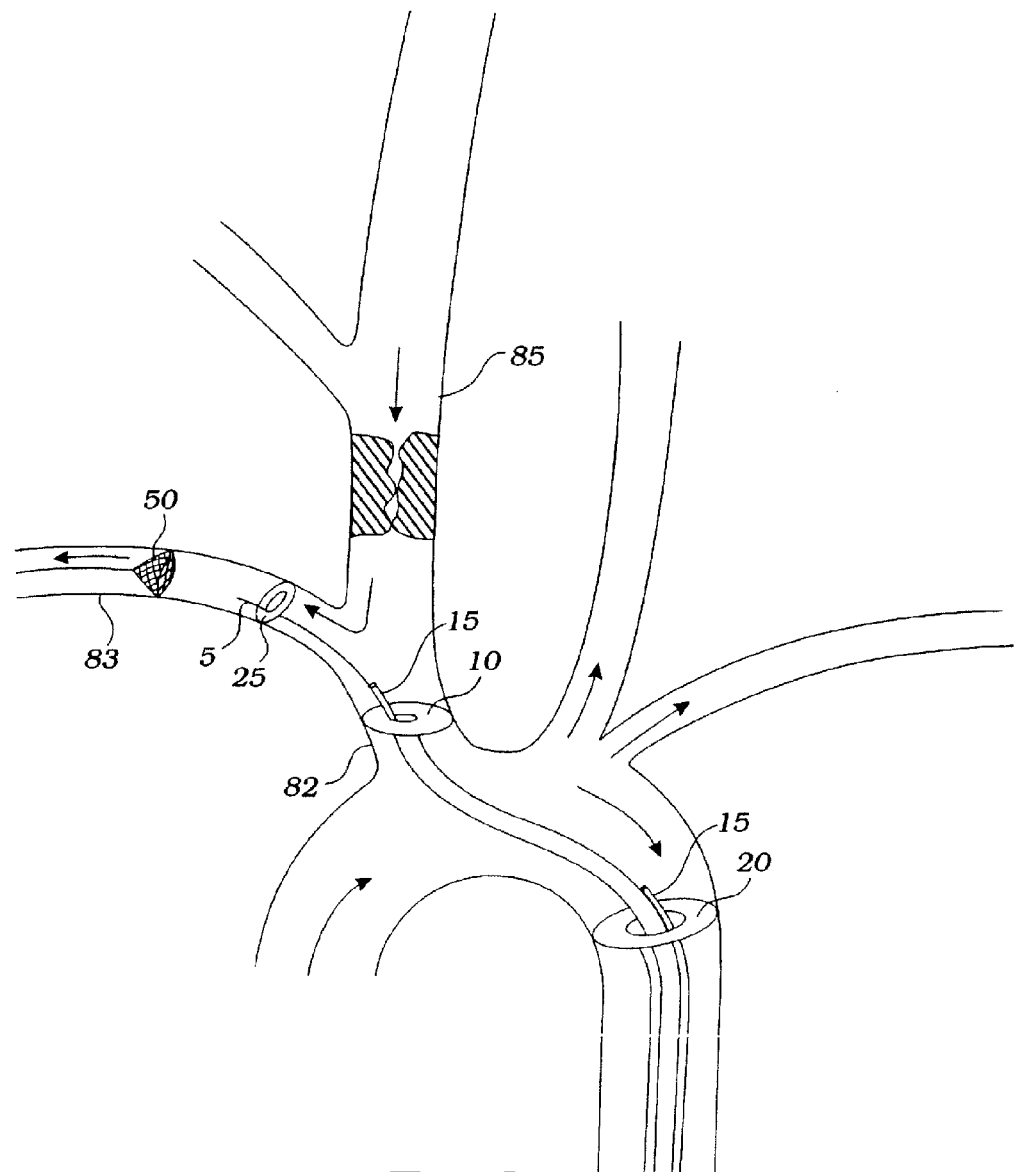
FIG. 8A depicts the method shown in FIG. 8 with a filter inserted in the right subclavian artery in a retrograde direction.

If flow reversal does not occur due to insufficient blood flow from contralateral circulation to the CCA, i.e., an insufficient pressure gradient between the CCA and the subclavian artery, a third constricting member 25 mounted distal to constrictor 10 can be used in certain embodiment to further increase the pressure gradient between the CCA and the subclavian artery as shown in FIG. 8. In use, the distal end of the device is inserted into right brachiocephalic artery 82. The separation between occluder 10 and constrictor 25 is adjusted to ensure proper placement in the respective arteries. Preferably, occluder 10 is slowly expanded by injection through inflation lumen 11 to constrict brachiocephalic artery 82, causing progressive decline of pressure in the subclavian artery. Constrictor 20 in the aorta is then expanded slowly to increase blood flow to the left CCA and left subclavian artery to augment collateral blood flow down right CCA 85. The pressure in the subclavian artery distal to constrictor 10, the pressure in the subclavian artery distal to constrictor 25, and the aortic pressure distal to constrictor 20 can be measured by manometers 15. At a critically low pressure in the distal brachiocephalic artery, blood flow in CCA 85 reverses toward the brachiocephalic artery and into the subclavian artery. The reversal of blood flow down the CCA and up the subclavian artery can be verified fluoroscopically with dye. If flow reversal does not occur due to insufficient pressure gradient between the CCA and the subclavian artery, constrictor 25 is gradually expanded to further reduce the pressure in the subclavian artery to create a more favorable pressure gradient between the CCA and the subclavian artery to reverse blood flow into the subclavian artery. Filter 50 may be inserted retrograde in right subclavian artery 83 as shown in FIG. 8A to prevent distal embolization in the right arm.

Figure 9:
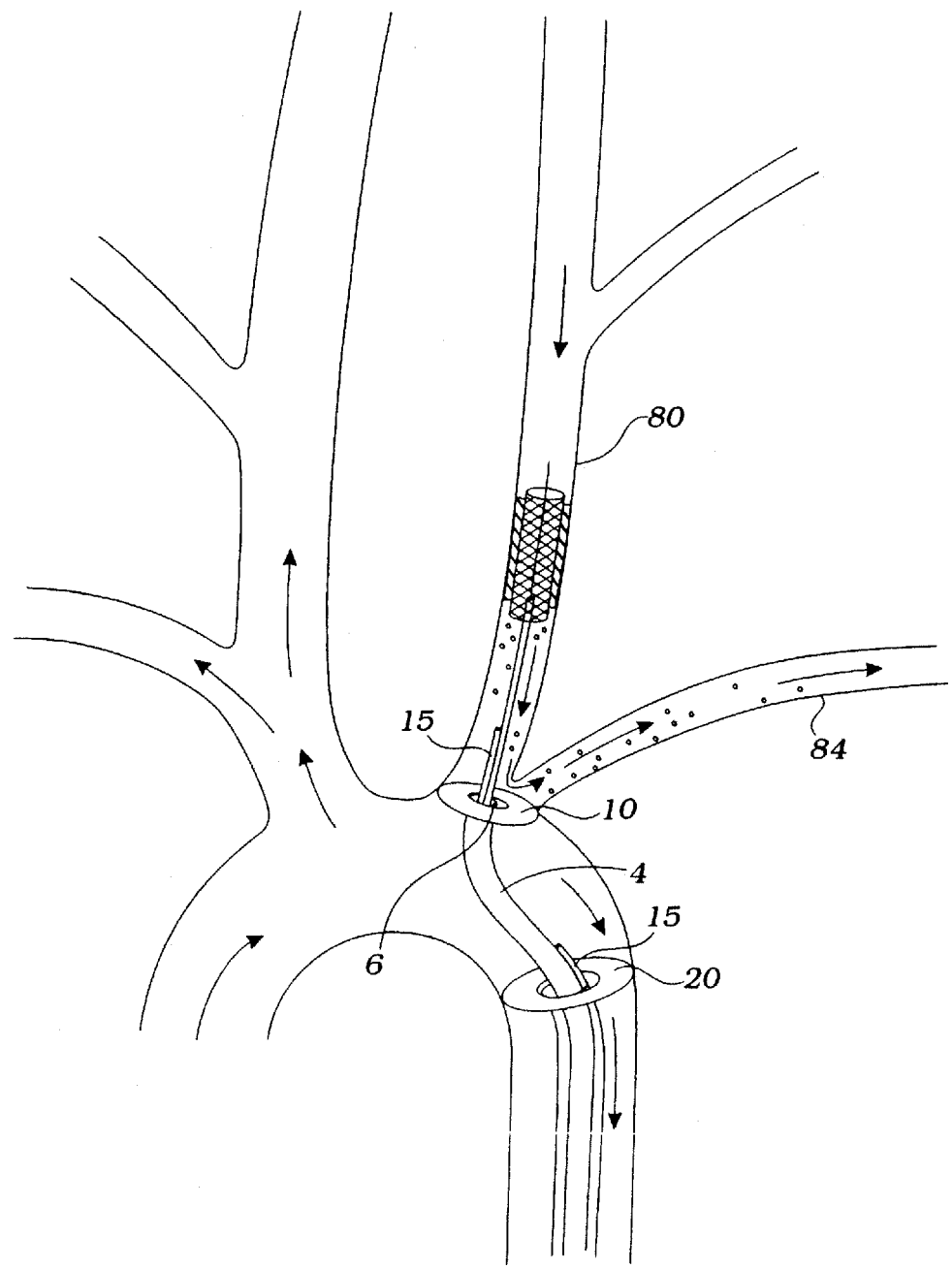
FIG. 9 depicts the constricting members of the device of FIG. 5B constricting the descending aorta and the inlets of the left common carotid artery and the left subclavian artery.
Figure 9A:
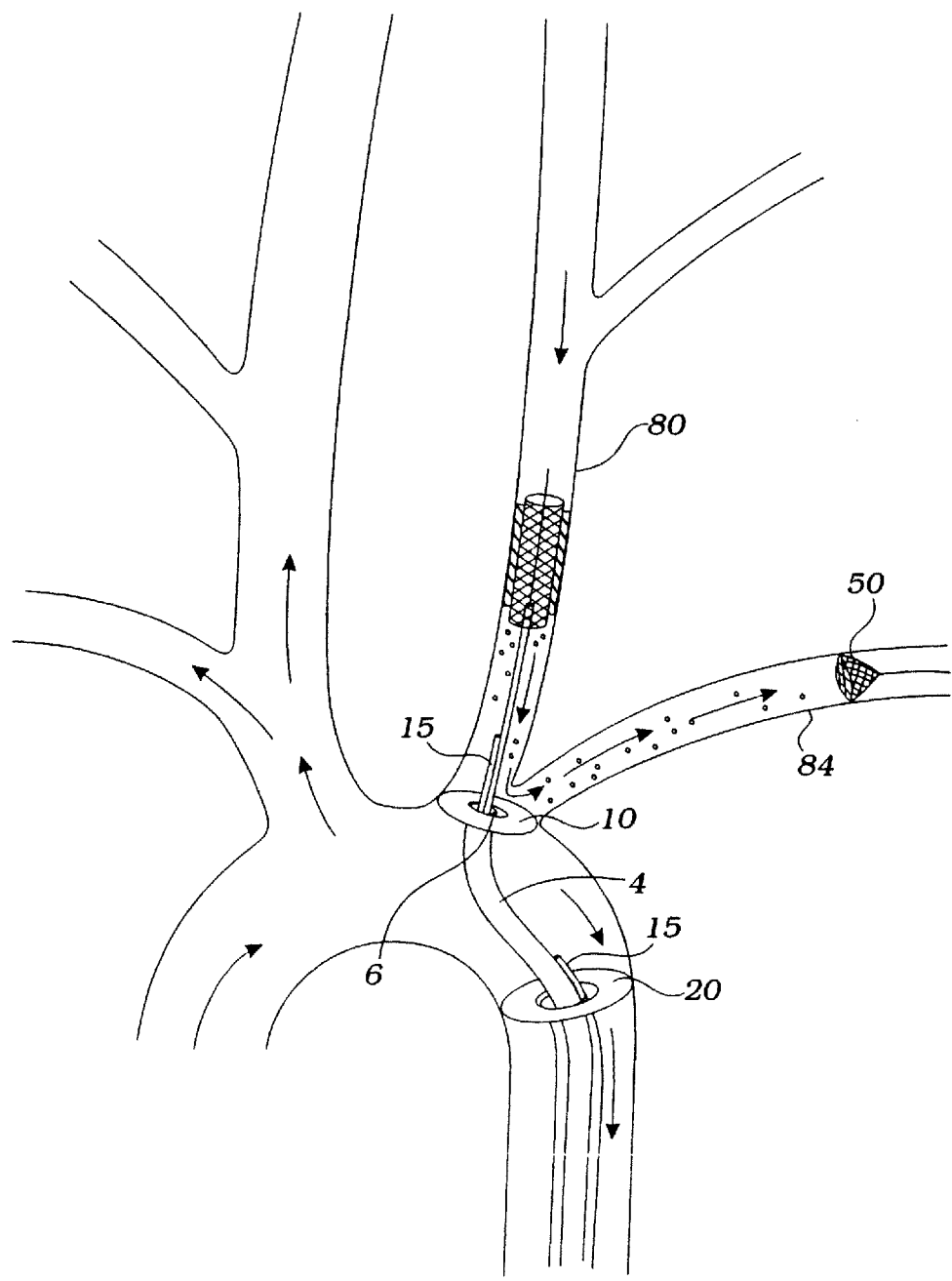
FIG. 9A depicts the method shown in FIG. 9 with a filter inserted in the left subclavian artery in a retrograde direction.

In treating an occluding lesion in the left common carotid artery, the distal end of the device of FIG. 5B is shown inserted in the inlets of left CCA 80 and left subclavian artery 84 as depicted in FIG. 9. Occluding member 10 is expanded to limit blood flow from the aorta into the left CCA and the left subclavian artery. Constrictor 20 is also expanded slowly to cause an increase in blood flow to the right brachiocephalic artery, right CCA, and right subclavian artery, thereby augmenting collateral blood flow down left CCA 80 via the circle of Willis. After blood flow reverses from left CCA 80 and into left subclavian artery 84, a therapeutic instrument, such as a stent is inserted through the lumen of elongate tubular member 4 and port 6. The stent is shown deployed over the atheromatous lesion in left CCA 80, thereby compressing the lesion and enlarging the luminal diameter. With reversal of blood flow from the CCA to the subclavian artery, distal embolization of debris generated by compression of the atheromatous lesion to the intracranial cerebral arteries is avoided, thereby minimizing risk of ischemic stroke. In FIG. 9A, filter 50 may be inserted in left subclavian artery 84 in a retrograde direction to prevent embolization to the arteries of the left arm.

Figure 10:
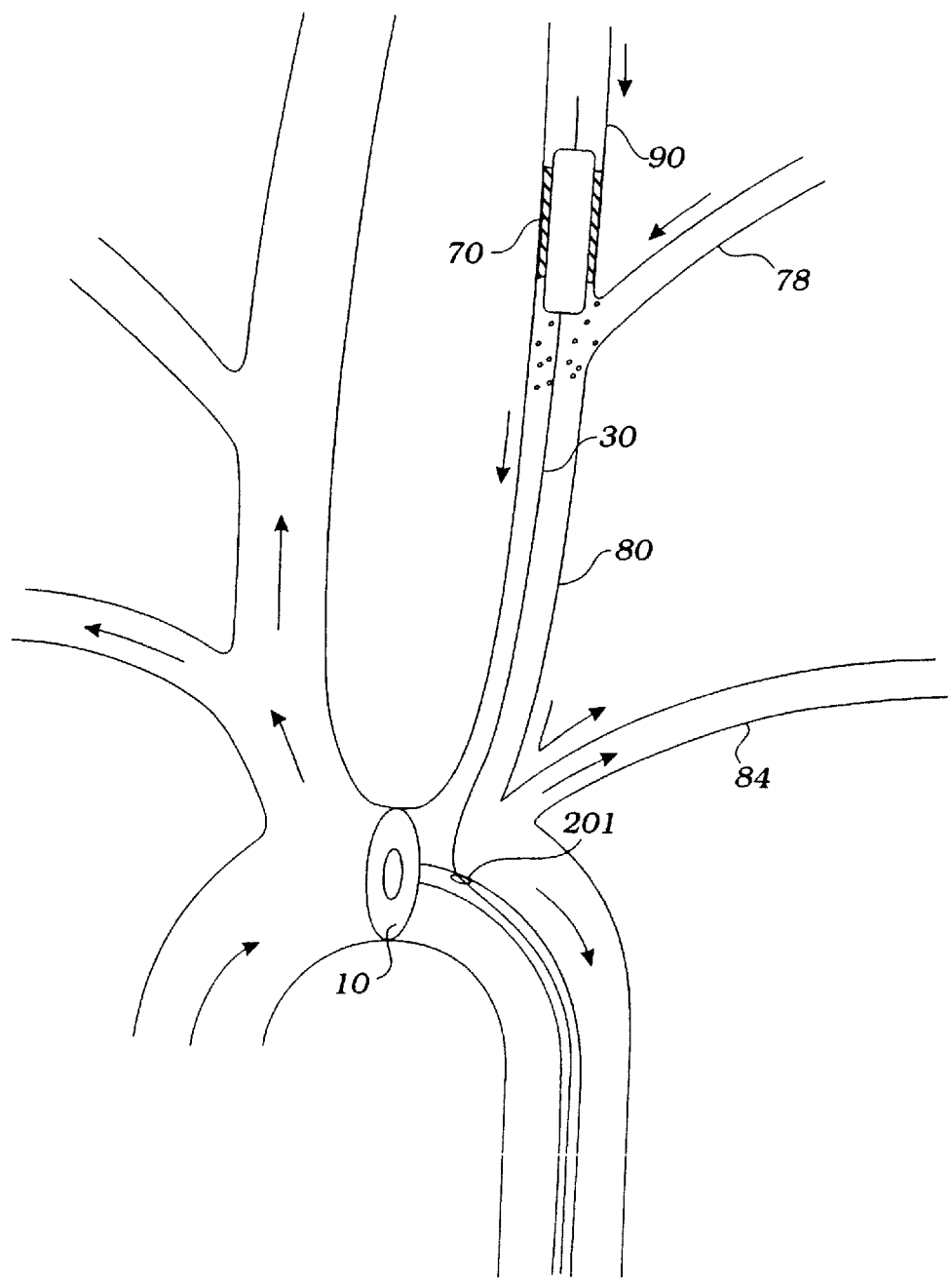
FIG. 10 depicts an aortic constriction catheter capable of causing flow reversal down the left CCA.
Figure 10A:
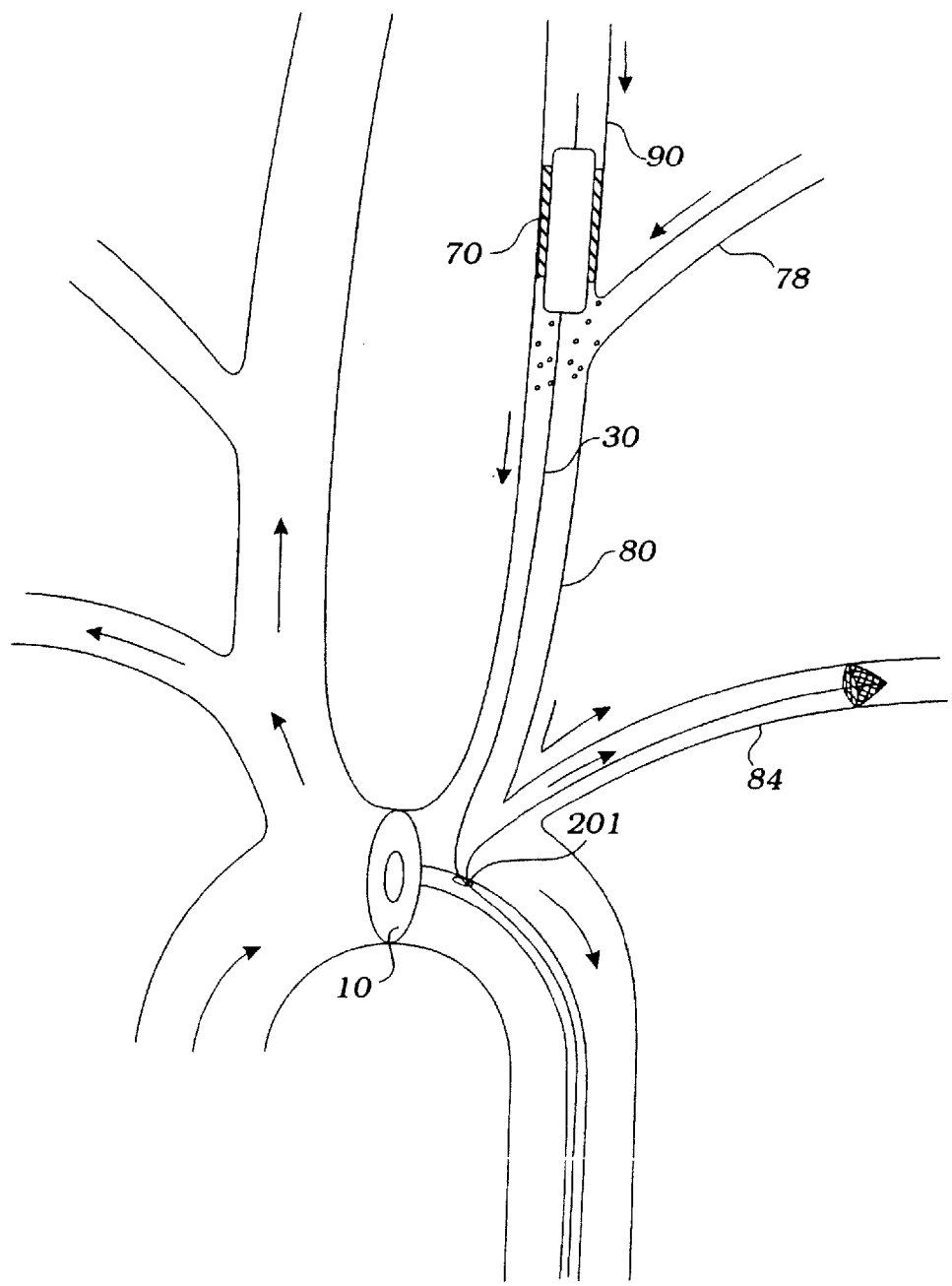
FIG. 10A depicts a filter inserted through the catheter of FIG. 10 and deployed in the left subclavian artery to capture embolic debris.

Flow reversal from left CCA 80 to left subclavian 84 can also be accomplished by placing constricting member 10 of device FIG. 4B in the aorta between the brachiocephalic artery and the left CCA as shown in FIG. 10. After flow reversal is accomplished, angioplasty catheter 30 is deployed through port 201 to access lesion 70. In FIG. 10A, filter 50 may be inserted through port 201 and expanded to capture embolic debris traveling to left subclavian artery 84.

Figure 11:
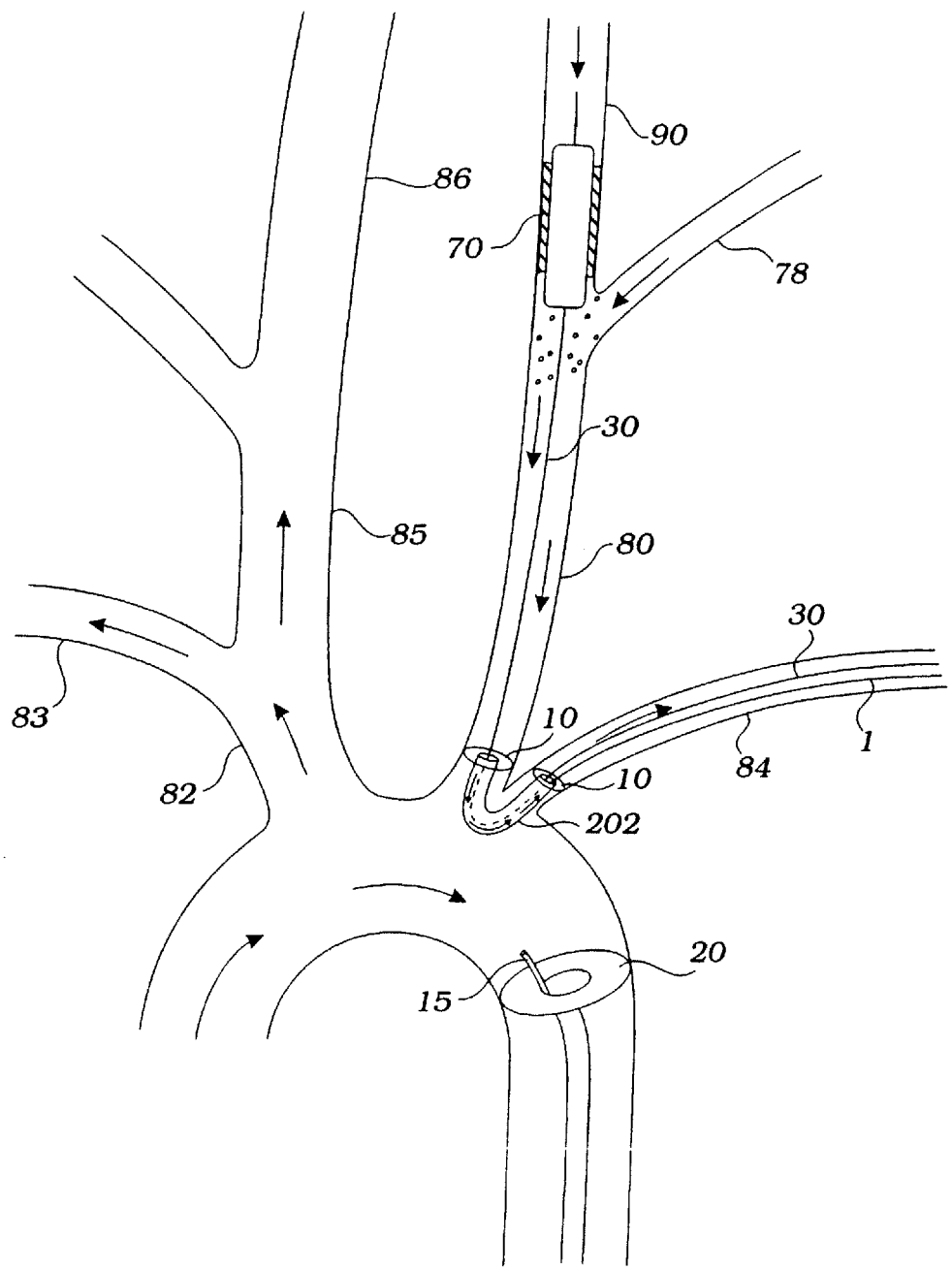
FIG. 11 depicts treatment of a left internal carotid lesion using aortic coarctation and an occlusion catheter capable of bridging between the left common carotid artery and the left subclavian artery.
Figure 11A:
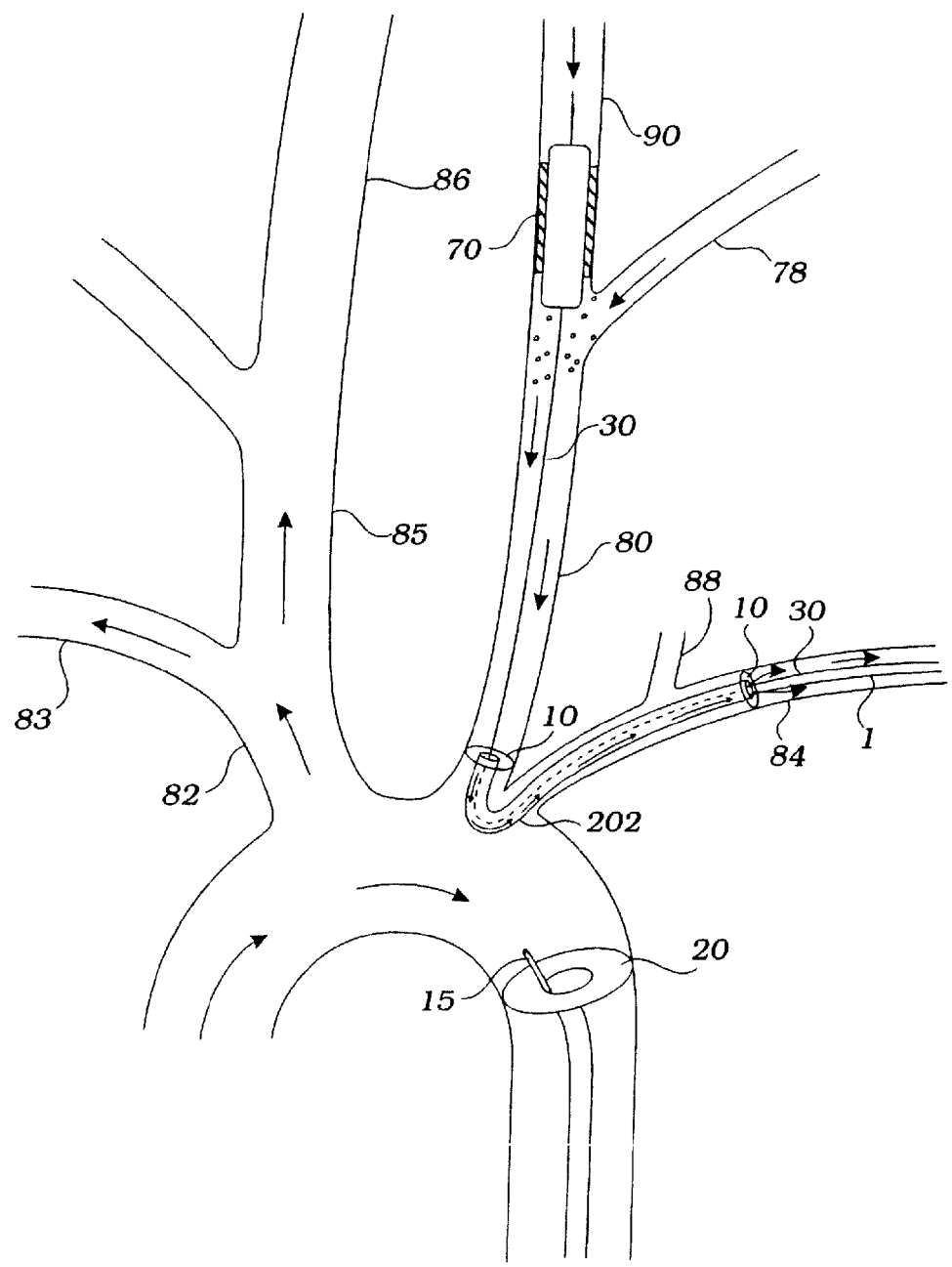
FIG. 11A depicts treatment of a left internal carotid lesion using aortic coarctation and an occlusion catheter capable of bridging between the left CCA and the left subclavian artery downstream of the left vertebral artery to prevent embolization into the left vertebral artery.
Figure 11B:
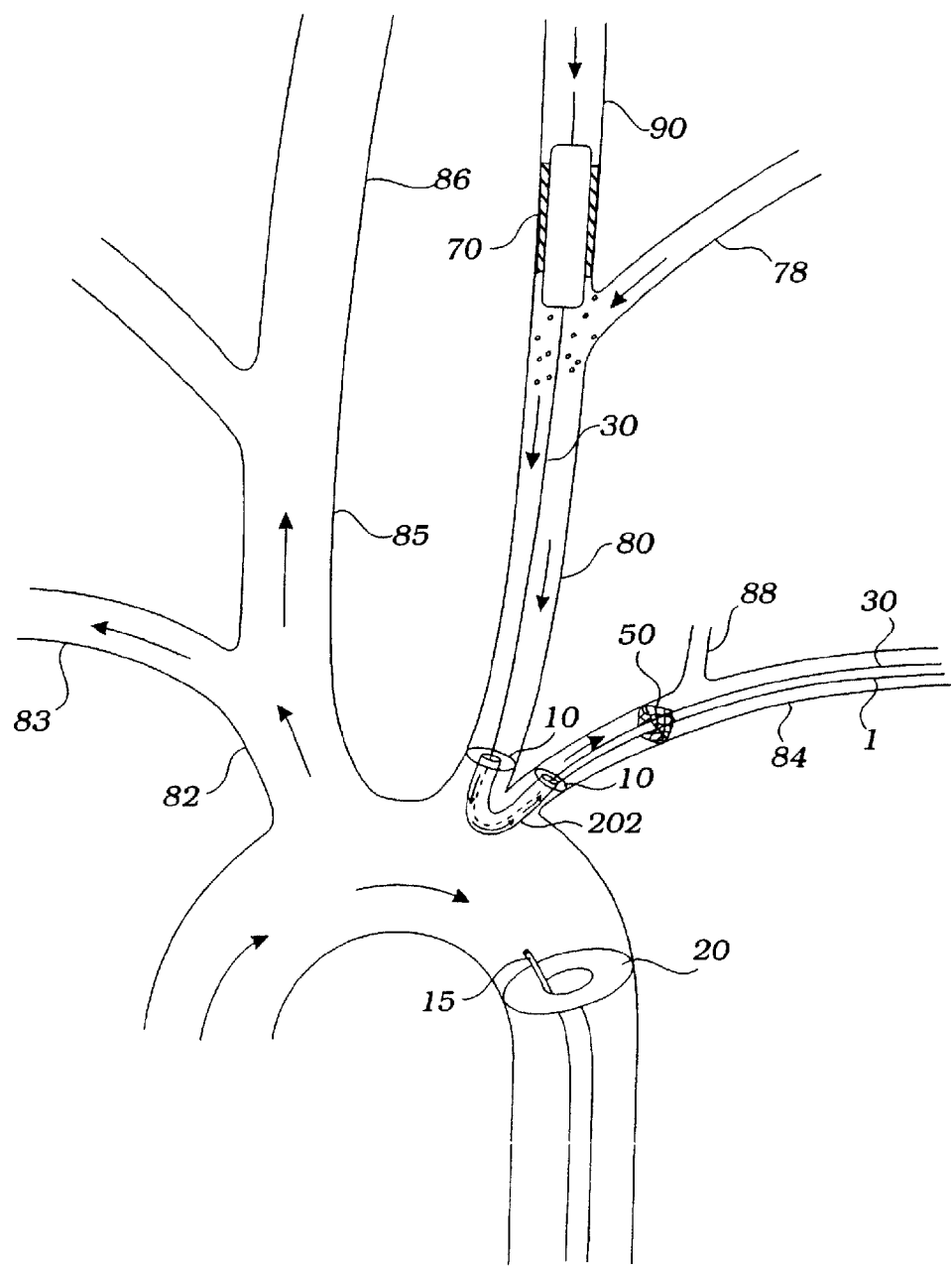
FIG. 11B depicts a filter mounted on the catheter of FIG. 11 and expanded in the right subclavian artery upstream the takeoff of the left vertebral artery to capture embolic debris.

FIG. 11 depicts an alternative embodiment wherein first and second occluding members 10 are expanded to occlude each of the left CCA and left subclavian artery. This device is introduced, for example, through the left subclavian artery. Flow reversal from left CCA 80 to left subclavian artery 84 is established through tubular member 202 mounted at the distal end of catheter 1. Expansion of constrictor 20 placed in the descending aorta increases blood flow to right brachiocephalic artery 82, right CCA 85, and right subclavian artery 83 and facilitates flow reversal from left CCA 80 to left subclavian artery 84. Interventional catheter 30 is deployed through tubular member 202 into left CCA 80. In FIG. 11A, second occluding member 10 is located in the left subclavian artery downstream of the left vertebral artery to prevent embolization into the left vertebral artery. Alternatively, optional filter 50, mounted on catheter 30 or catheter 1, is positioned and expanded in left subclavian artery 84 upstream the takeoff of left vertebral artery 88 as shown in FIG. 11B to prevent embolic debris from traveling distally into the left vertebral artery and the left subclavian artery.

Figure 12A:
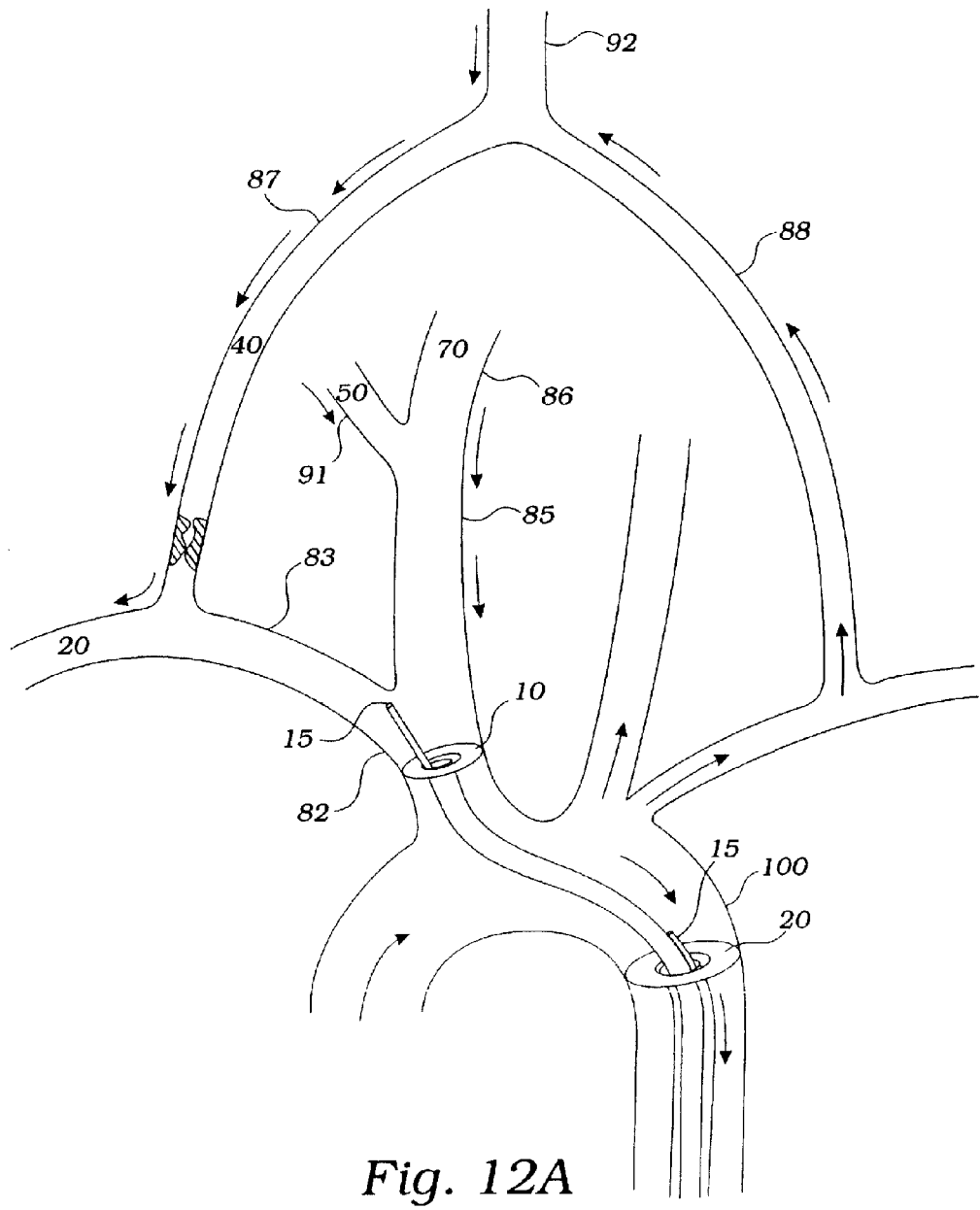
FIG. 12A depicts the device of FIG. 5 inserted in the right brachiocephalic artery through the descending aorta to treat a lesion in the right vertebral artery.
Figure 12B:
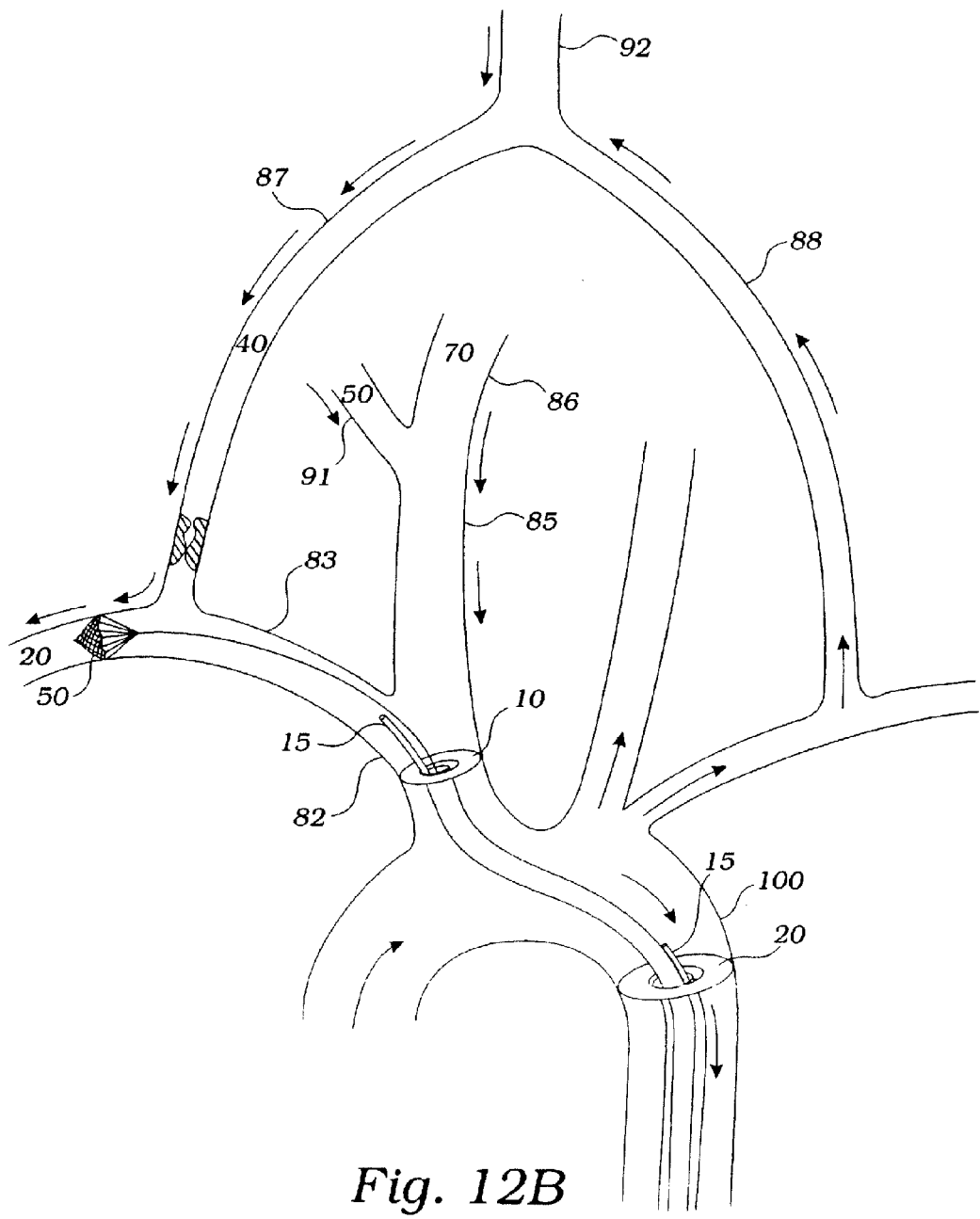
FIG. 12B depicts a filter inserted through the catheter of FIG. 12A in the right subclavian artery to prevent distal embolization.

Flow reversal from the right vertebral artery having an occluding lesion down the ipsilateral subclavian artery can also be achieved by placing a constrictor in the ipsilateral brachiocephalic artery and a constrictor in the descending aorta as shown in FIG. 12A. The distal end of the device of FIG. 5B is inserted and advanced into right brachiocephalic artery 82 upstream the takeoff of right common carotid artery 85. Constricting member 10 is slowly expanded, causing a reduction in the blood pressure (to approximately 20 mmHg) downstream the constrictor. As a result, a favorable pressure gradient is created between the right vertebral artery distal to the occluding lesion (typically having pressure of approximately 40 mmHg) and the subclavian artery, causing reversal of blood flow from the vertebral artery into the subclavian artery. Reversal of blood flow from right common carotid artery 85 into the subclavian artery also occurs due to the pressure differential between the CCA and the subclavian artery. Expansion of constrictor 20 in descending aorta 100 further increases the pressure gradient between the right vertebral artery distal to the occluding lesion and the right subclavian artery by increasing collateral blood flow to the occluded right vertebral artery 87 through increasing blood flow to left vertebral artery 88 and the left CCA via circle of Willis. Filter 50, as shown in FIG. 12B, may be inserted through the catheter and expanded in right subclavian artery 83 to prevent embolic debris from traveling downstream to the right arm.

Figure 12C:
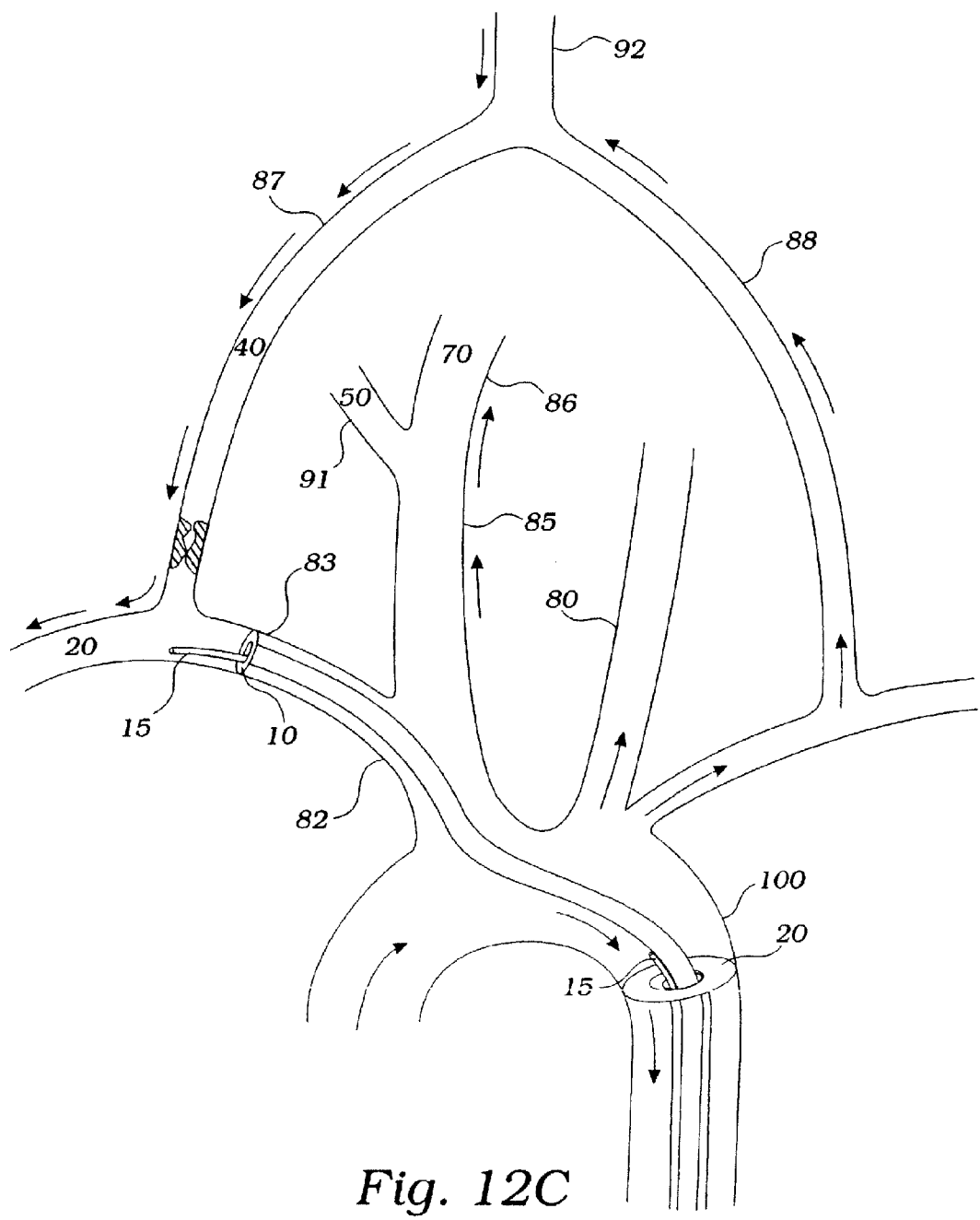
FIG. 12C depicts the device of FIG. 5 inserted in the right subclavian artery through the descending aorta to treat a lesion in the right vertebral artery.
Figure 12D:
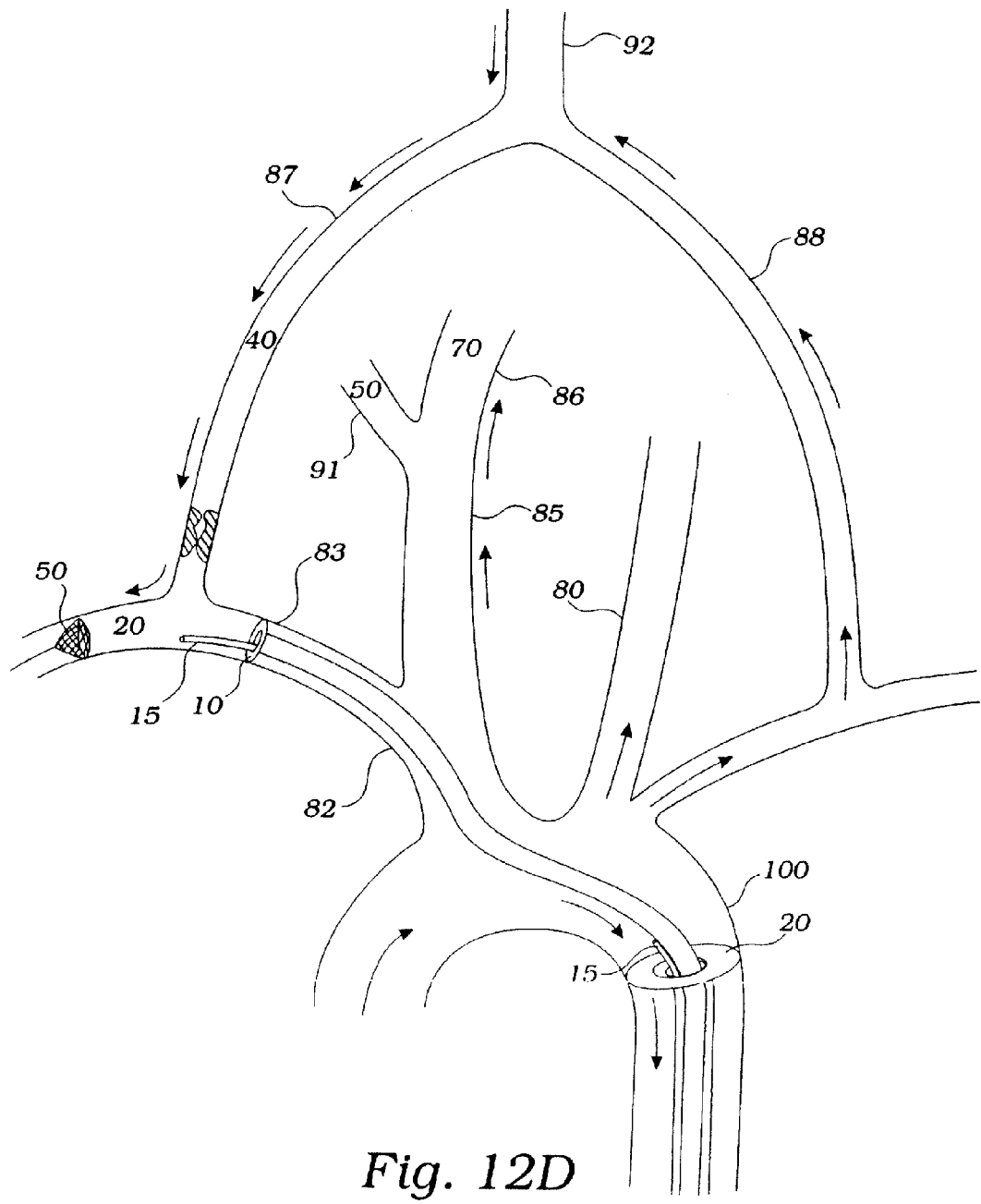
FIG. 12D depicts the method shown in FIG. 12C with a filter inserted in the right subclavian artery in a retrograde direction to prevent distal embolization.

Alternatively, reversal of blood flow down an occluded right vertebral artery can be achieved by inserting the distal end of the device of FIG. 5B in right subclavian artery upstream the takeoff of the right vertebral artery as depicted in FIG. 12C. Constricting member 10 is slowly expanded to constrict subclavian artery 83, causing progressive decline in the blood pressure of the subclavian artery downstream the constrictor. The pressure in the subclavian artery distal to the constrictor can be measured by manometer 15. Constrictor 20 is expanded in descending aorta 100 to augment blood flow to left CCA 80 and left subclavian artery 88 and down right vertebral artery 87 via the collateral circulation. The reversal of blood flow down the vertebral artery into the subclavian artery can be verified fluoroscopically with dye. After blood reversal is established, therapeutic devices, such as an atherectomy, angioplasty, and/or stenting catheter, can then be inserted through the lumen of the constricting device, or through any other suitable percutaneous entry point, and advanced to treat the occluding lesion. With reversal of blood flow down the vertebral artery into the subclavian artery, distal embolization to the intracranial arteries is avoided, thereby minimizing risk of stroke. Distal embolization of the branches of the subclavian artery that supply the extremity has far less devastating consequences than the arterial branches which supply the brain stem. In FIG. 12D, optional filter 50 may be inserted in right subclavian artery 83 in a retrograde direction to capture embolic debris.

Figure 12E:
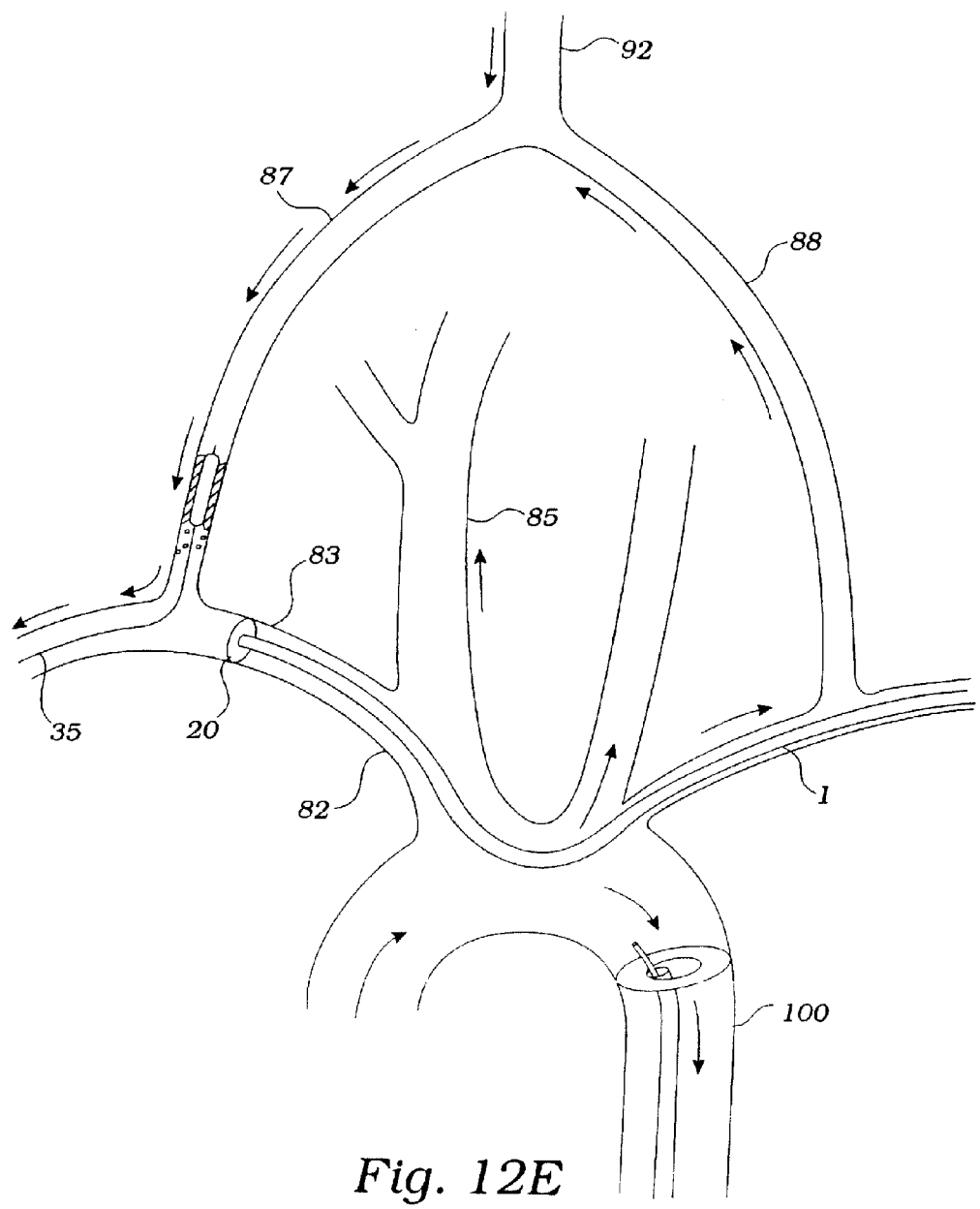
FIG. 12E depicts treatment of a lesion in the right vertebral artery using an occlusion catheter inserted through the left subclavian artery and a constrictor catheter inserted in the descending aorta.
Figure 12F:
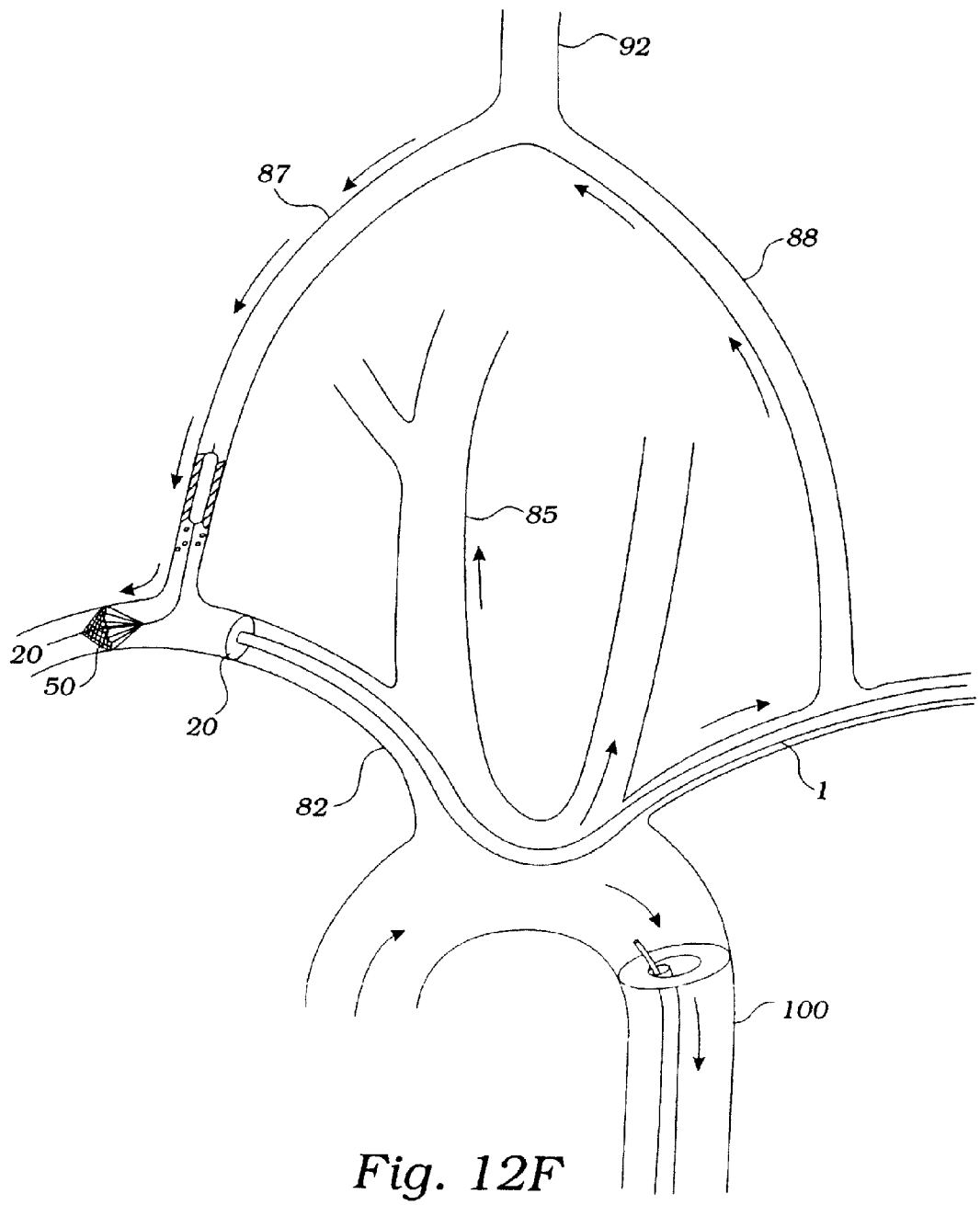
FIG. 12F depicts a filter mounted on an angioplasty catheter of FIG. 12E in the right subclavian artery to prevent distal embolization.

Reversal of blood flow down an occluded right vertebral artery can also be achieved by inserting the occlusion catheter of FIG. 4A in right subclavian artery upstream the takeoff of the right vertebral artery through the left subclavian artery as shown in FIG. 12E. Angioplasty catheter 35 can be inserted through the lumen of catheter 1 or through the right subclavian artery as shown. Angioplasty catheter 35 may also include filter 50 as shown in FIG. 12F which is deployed in right subclavian artery 83 to capture embolic debris. After completion of the angioplasty procedure, filter 50 is collapsed and removed with the captured emboli, thereby preventing distal embolization to the right arm.

Figure 12G:
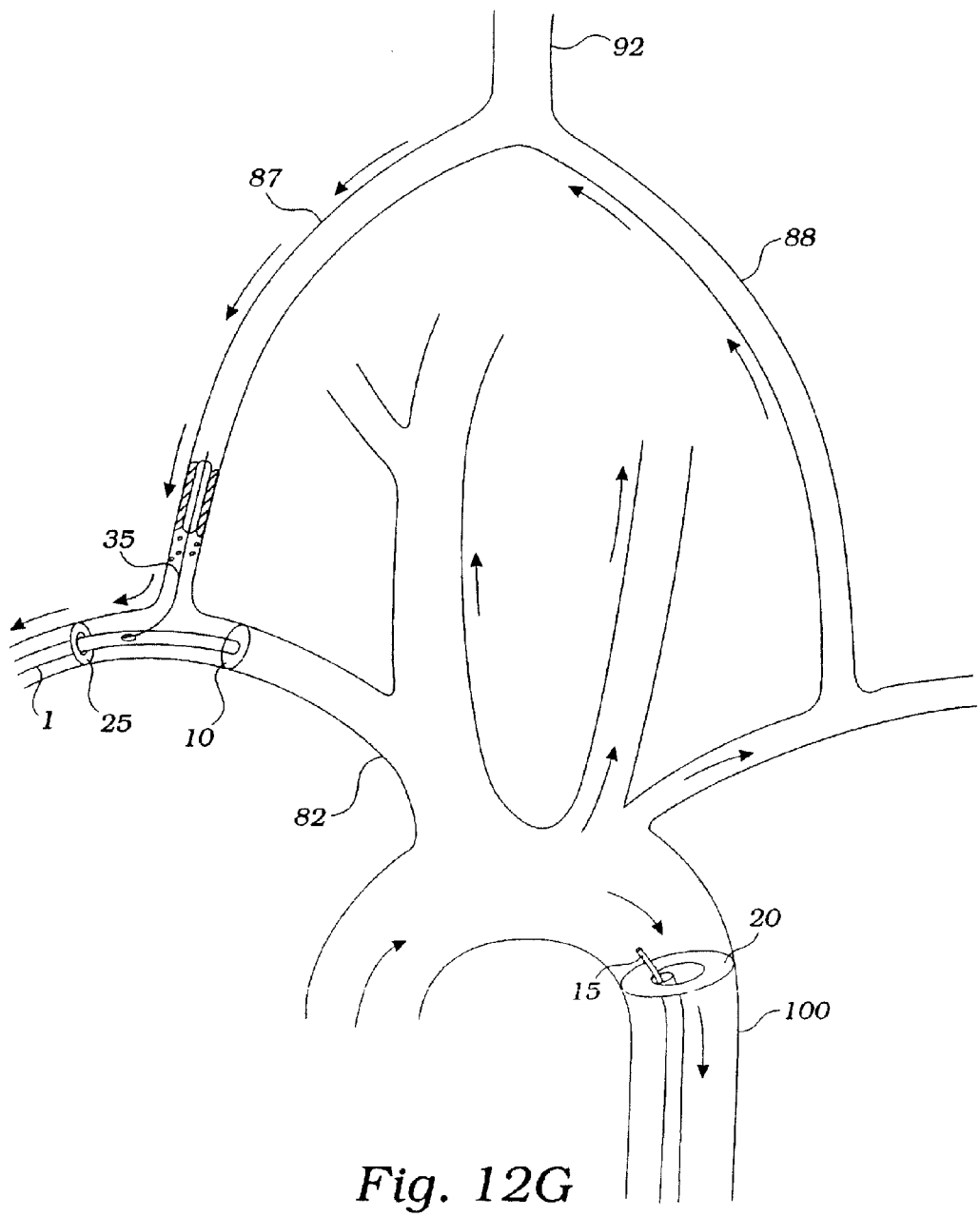
FIG. 12G depicts treatment of a lesion in the right vertebral artery using an occlusion catheter inserted through the right subclavian artery and a constrictor catheter inserted in the descending aorta.
Figure 12H:
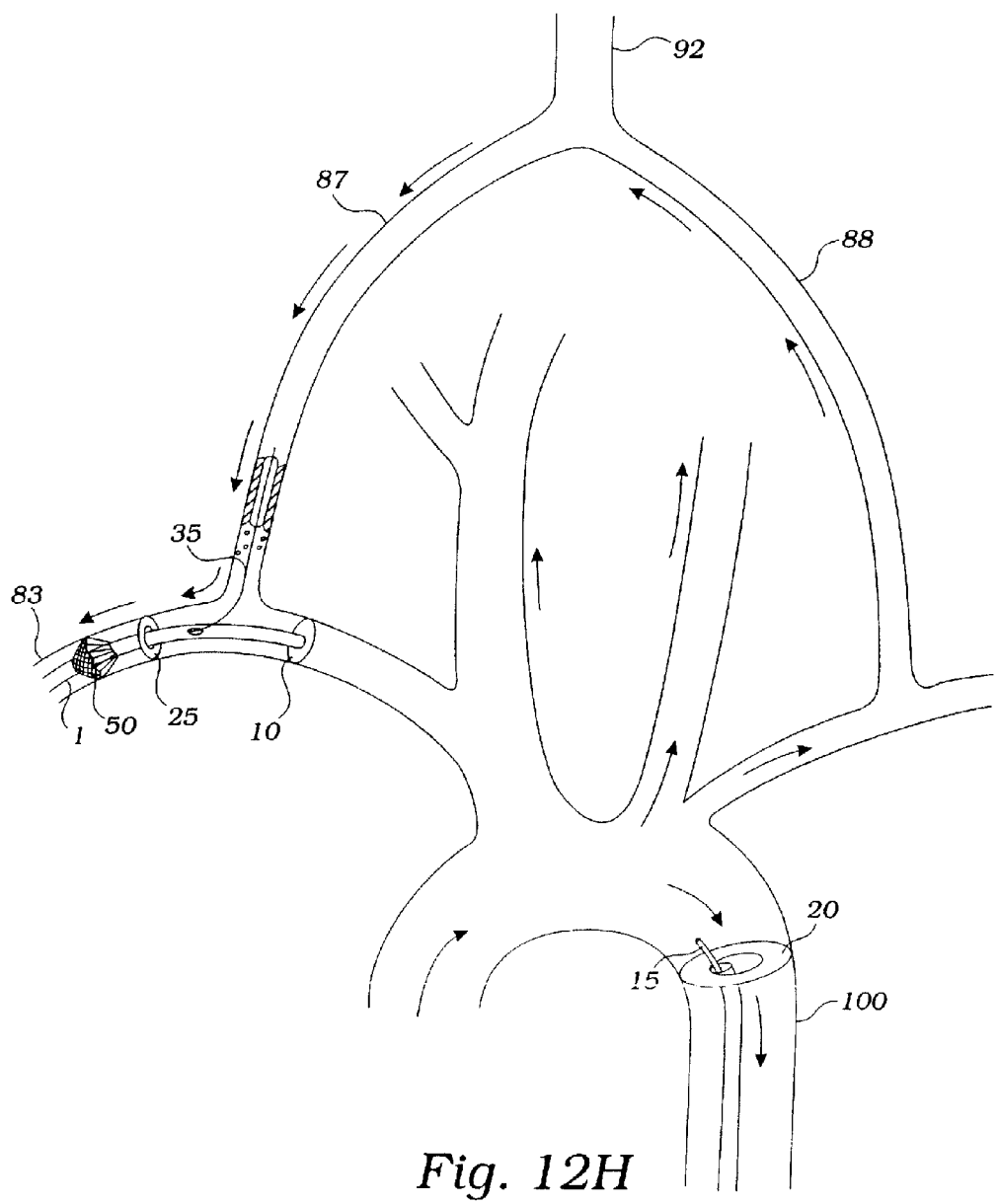
FIG. 12H depicts a filter mounted on the catheter of FIG. 12G in the right subclavian artery to prevent distal embolization.

In FIG. 12G, an embodiment having distal constrictor/occluder 10 and proximal constrictor/occluder 25 suitable for insertion in the subclavian artery is inserted in right subclavian artery 83 to further reduce pressure in the subclavian artery downstream the takeoff of right vertebral artery 87. Constricting/occluding member 10 is inserted and advanced in the subclavian artery downstream to the takeoff of right CCA 85 and constricting member 25 is advanced in the subclavian artery downstream to the takeoff of right vertebral artery 87. Constricting/occluding member 10 is first expanded to constrict/occlude the subclavian artery. Constrictor 20 of the device of FIG. 4B is inserted in the descending aorta and expanded to increase blood flow to the left CCA and left subclavian artery, thereby causing augmentation of collateral blood flow down right vertebral artery 87. If flow reversal does not occur due to insufficient blood flow from the right vertebral artery, i.e., insufficient pressure gradient between the right vertebral artery and the subclavian artery, constricting/occluding member 25 is expanded to further reduce the pressure in the subclavian artery to create an even more favorable pressure gradient to reverse blood flow into the subclavian artery from the vertebral artery. Catheter 1 may also include filter 50 as shown in FIG. 12H to capture embolic debris in right subclavian artery 83.

Figure 13:
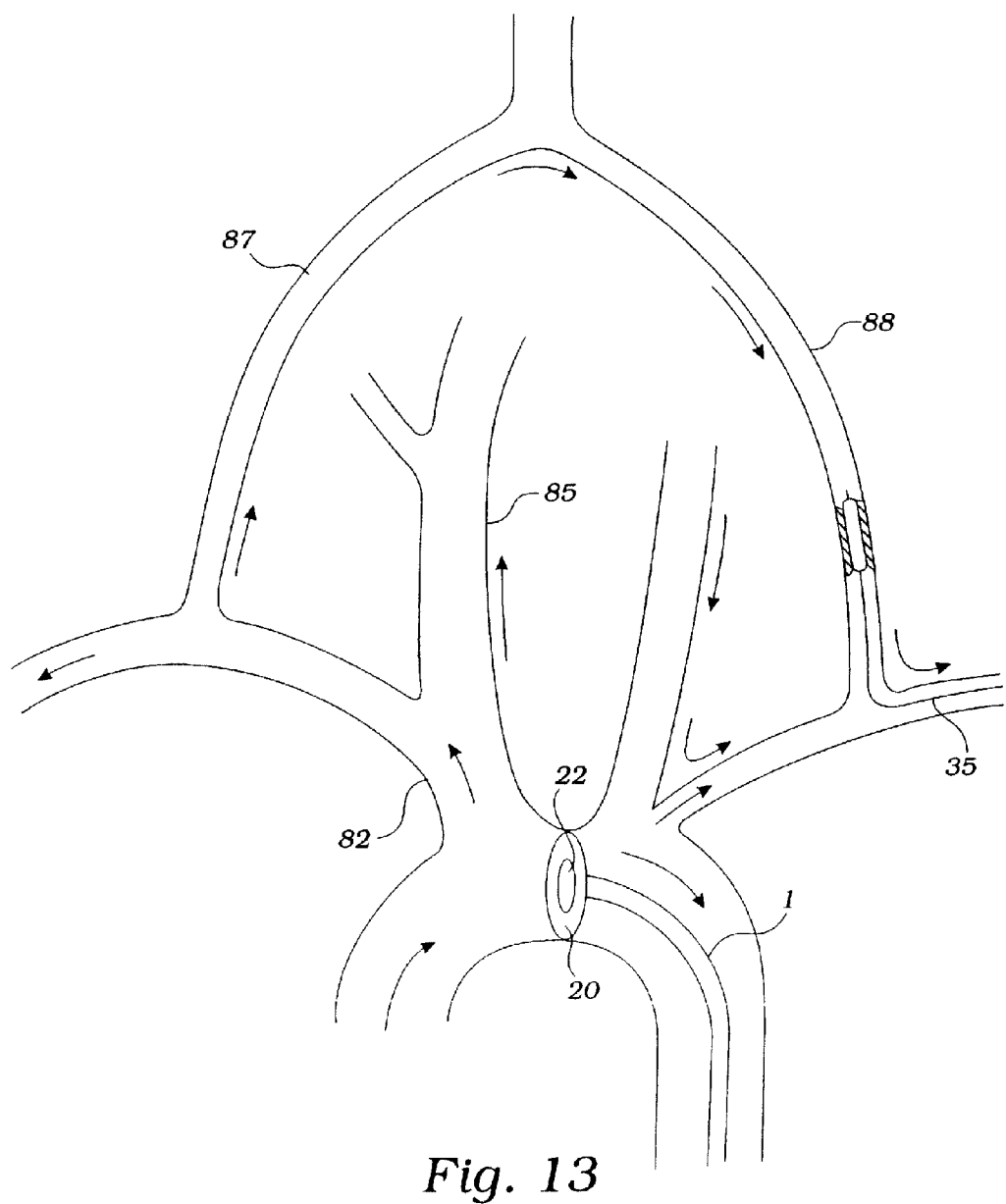
FIG. 13 depicts an aortic constriction catheter capable of causing flow reversal down the left vertebral artery.
Figure 13A:
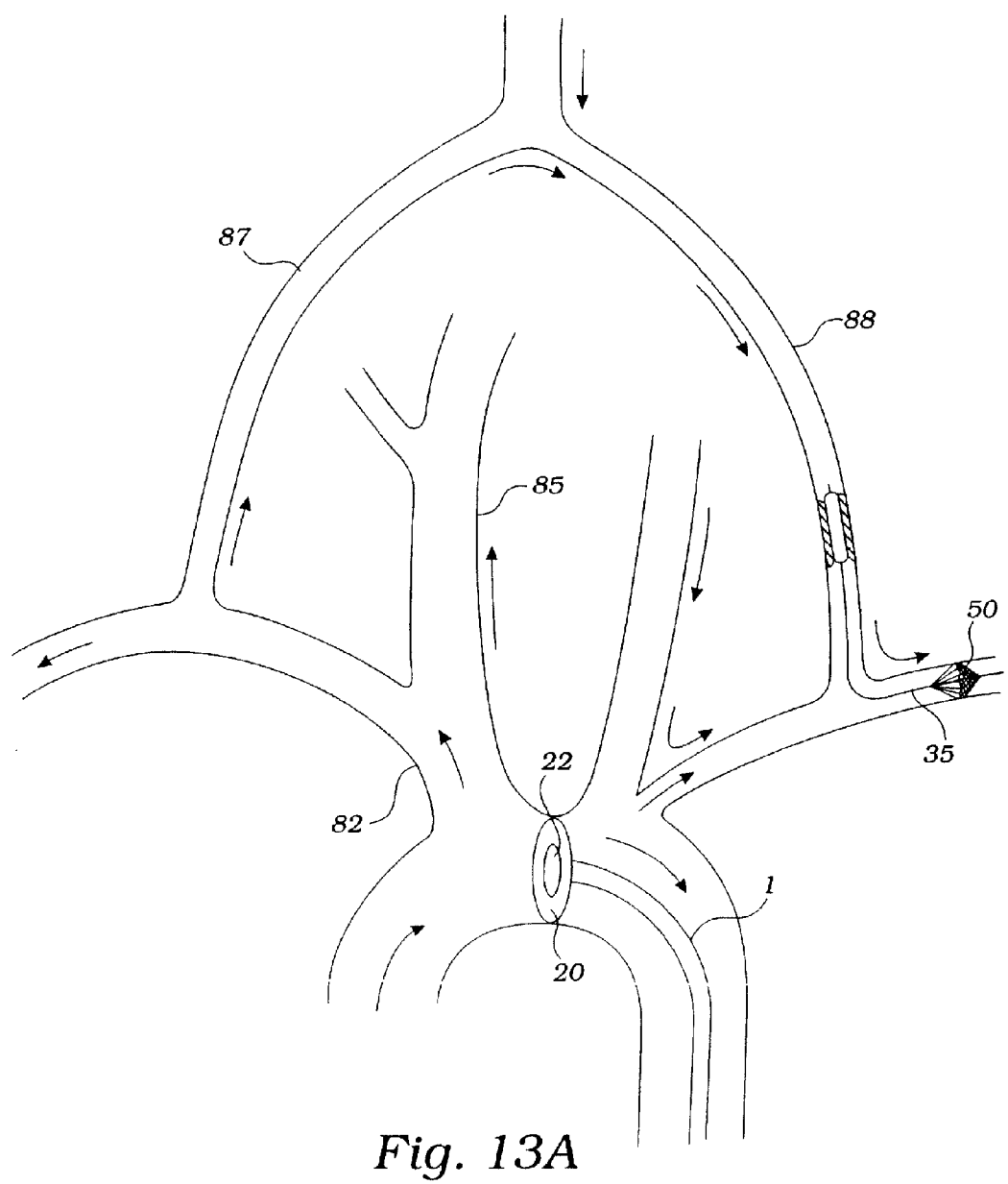
FIG. 13A depicts a filter mounted on the angioplasty catheter of FIG. 13 and expanded in the left subclavian artery to prevent distal embolization.

Reversal of blood flow down an occluded left vertebral artery 88 can also be accomplished by placing constrictor 20 in the aortic trunk between the takeoff of the right brachiocephalic artery and the left CCA as shown in FIG. 13. Collateral blood flow down left vertebral artery 88 is augmented by increased blood flow from the right brachiocephalic artery, right CCA, and right vertebral artery. After reversal of blood flow is established, angioplasty catheter 35 is inserted into left vertebral artery 88 through the left subclavian artery as shown to treat the occluding lesion. In this manner, embolic debris generated during the procedure is forced down the vertebral artery and into the left subclavian artery, thereby avoiding distal embolization to the posterior cerebral circulation. Alternatively, filter 50 may be mounted on catheter 35 as shown in FIG. 13A to capture embolic debris and prevent emboli from traveling distally into the left arm.

Figure 14:
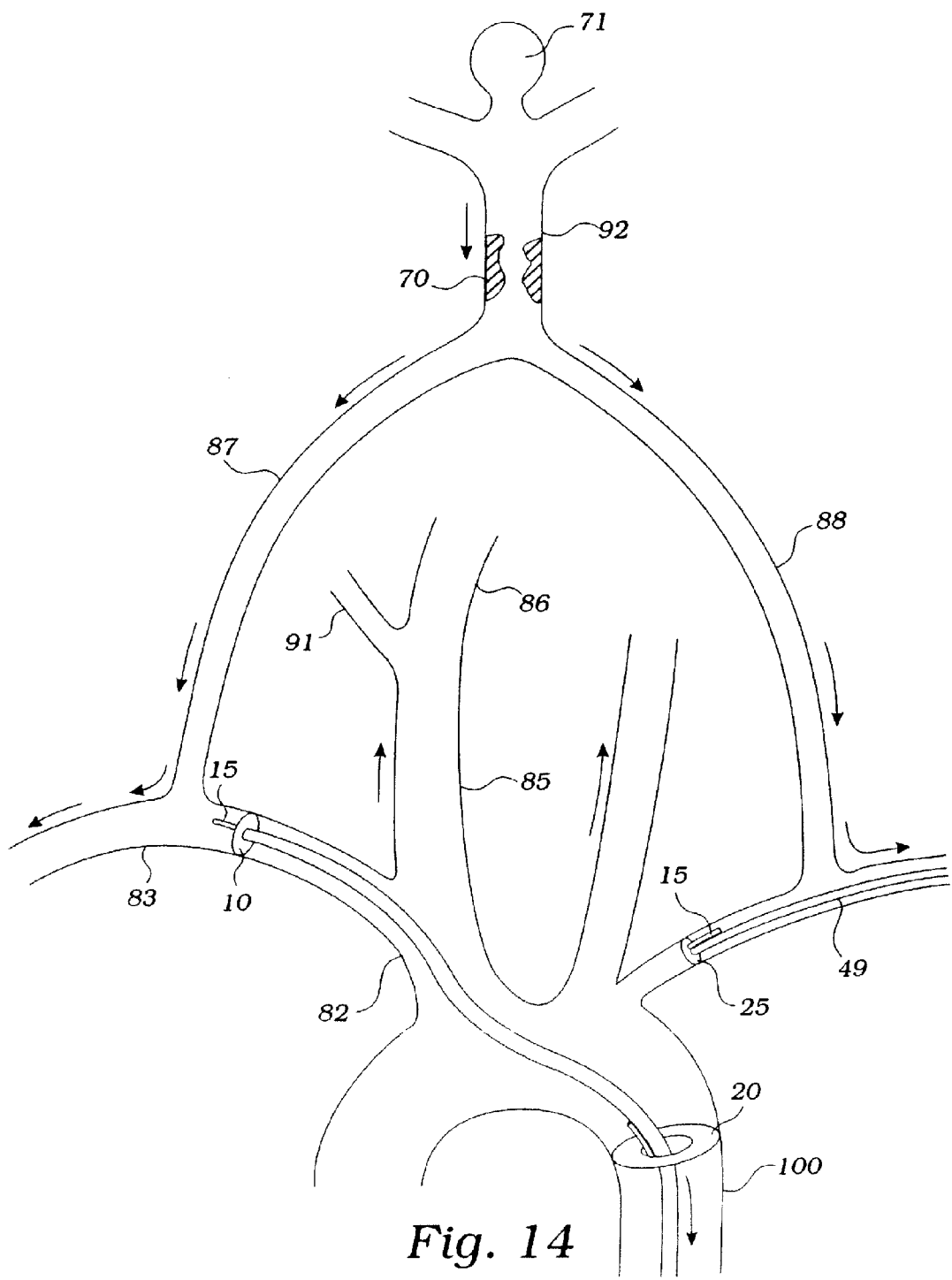
FIG. 14 depicts reversal of blood flow down the basilar artery using the device of FIG. 5C having the occlusion balloon positioned in the right subclavian artery, a coarctation balloon in the aorta, and a catheter having an occlusion balloon positioned in the left subclavian artery.
Figure 14A:
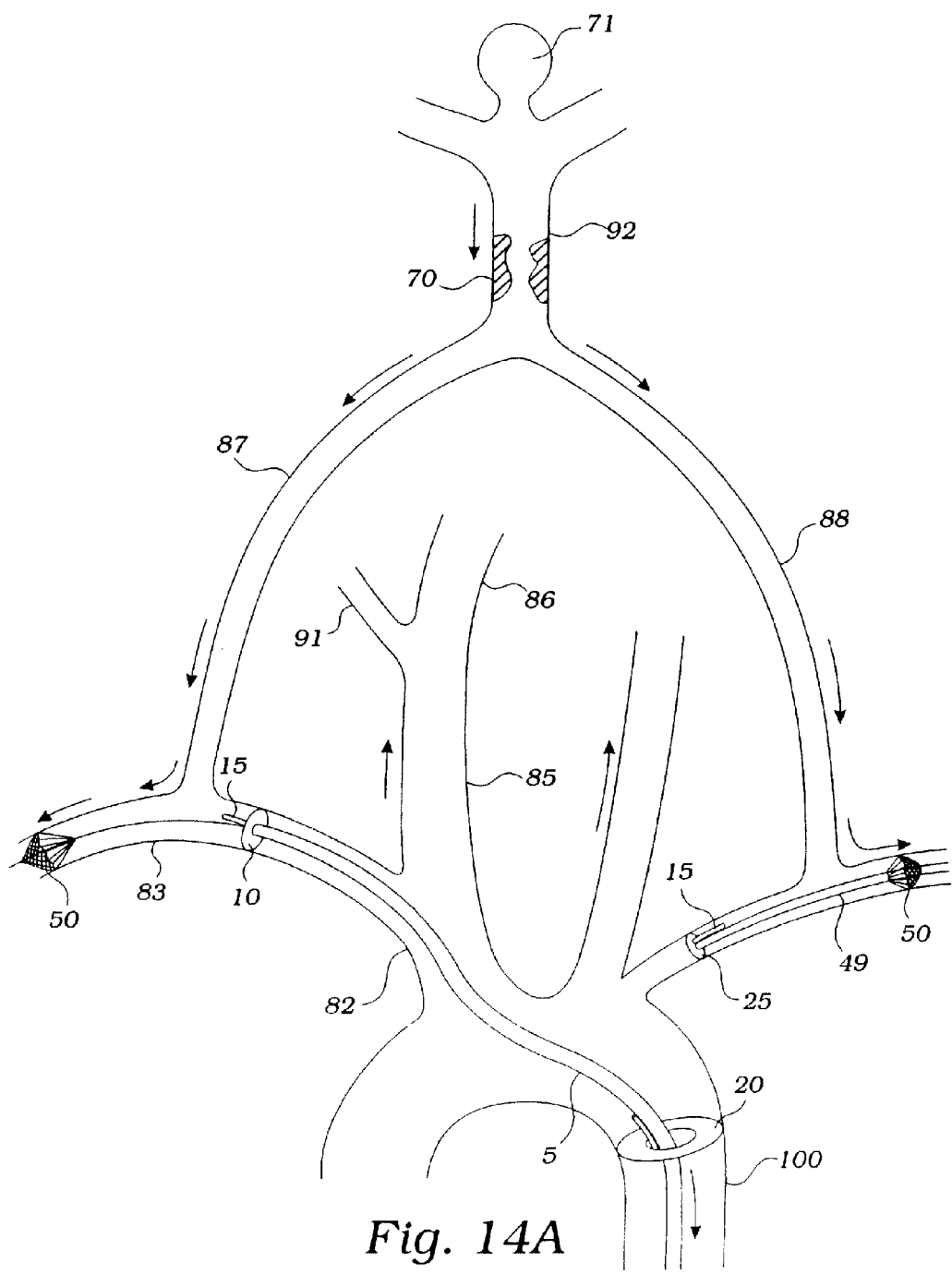
FIG. 14A depicts the method shown in FIG. 14 with filters expanded in the right and left subclavian arteries to prevent distal embolization to the arms.

In treating an occluding lesion in the basilar artery, reversal of blood flow from the basilar artery into the vertebral artery can also be accomplished by inserting a first constricting member in a vertebral artery and a second constricting member in the contralateral subclavian artery upstream the takeoff of the contralateral vertebral artery. Alternatively, first and second constricting members are placed in the right and left subclavian arteries upstream the takeoff of the respective vertebral arteries. For example, in FIG. 14, constricting member 10 of a device as in FIG. 5B is inserted in an antegrade direction into right subclavian artery 83 upstream the takeoff of right vertebral artery 87 through an incision on a peripheral artery, e.g., the femoral artery. Constricting member 20 is positioned in the descending aorta. Constricting member 25, mounted on catheter 49, is inserted in a retrograde direction into the left subclavian artery upstream the takeoff of left vertebral artery 88. Constricting members 10 and 25 are then expanded to constrict or occlude the subclavian arteries, causing a pressure drop in the vertebrobasilar junction. Constricting member 20 is slowly expanded to constrict the aorta to augment collateral circulation down the basilar artery by increasing blood flow to the right and left carotid arteries. After flow reversal is established, introduction of therapeutic device(s) into the basilar artery can be achieved through the lumen of either catheter. Embolic debris generated during the procedure(s) is diverted from the basilar artery into the vertebral arteries and into the subclavian arteries, thereby preventing devastating consequences of brainstem embolization. In FIG. 14A, first filter 50 may be inserted through lumen 5 of the catheter to deploy in right subclavian artery 83, and second filter 50 may be mounted on catheter 49 to expand in left subclavian artery 84 to prevent distal embolization to the right and left arms.

Figure 15A:
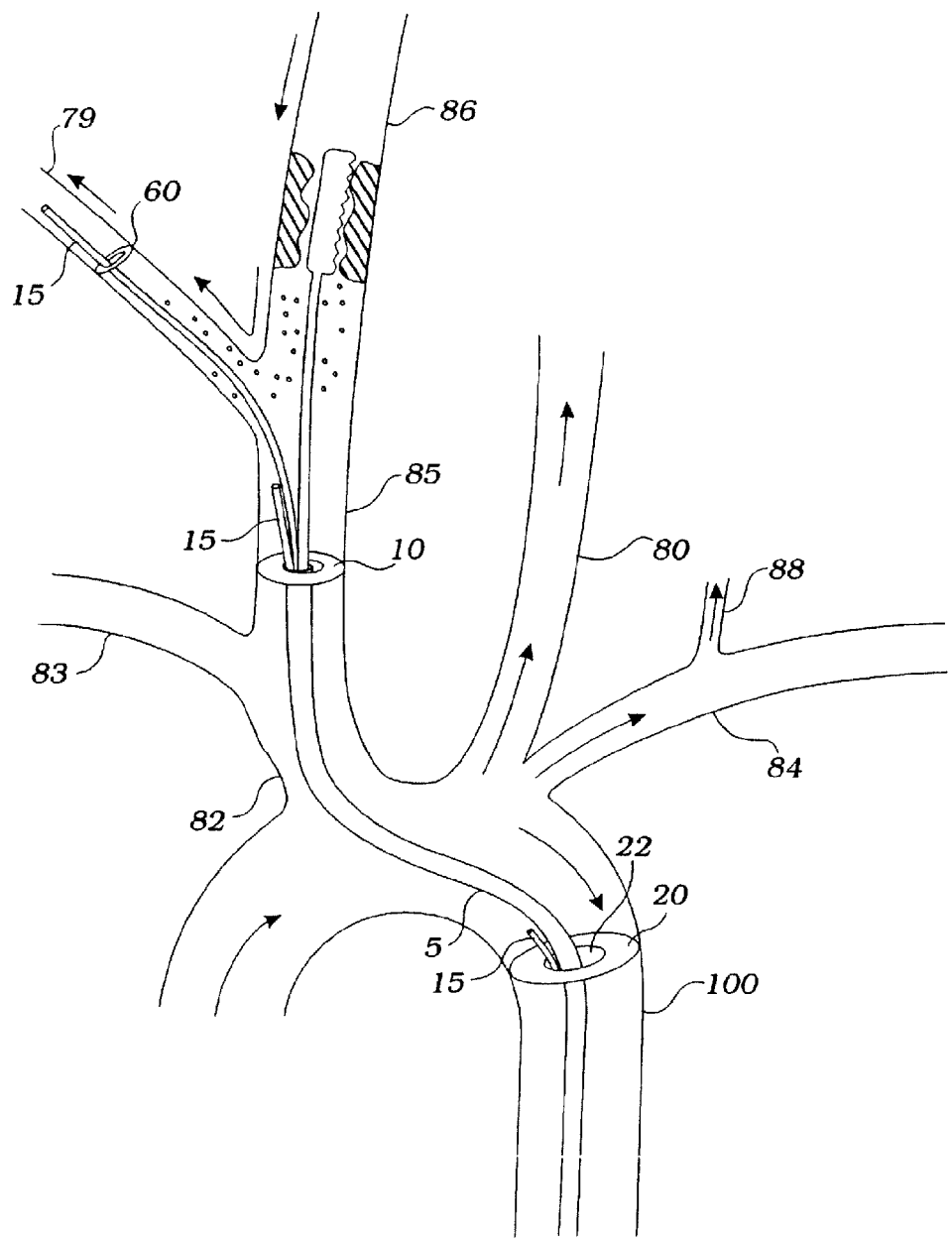
FIG. 15A depicts reversal of blood flow from the right internal carotid artery into the right external carotid artery during angioplasty of an internal carotid lesion.

An alternative method using the flow reversal concept in treating an occluding lesion in the right internal carotid artery is shown in FIG. 15A. The components of the device for use in the CCA and ECA are described in Barbut, U.S. Pat. No. 6,146,370, incorporated herein by reference in its entirety. The device includes first constricting member 20, second constricting or occluding member 10, and optionally third constricting member 60. Constricting member 60, when present, is inserted into right external carotid artery 79. Constricting or occluding member 10 is positioned in right common carotid artery 85, and constricting member 20 is positioned in the descending aorta. Preferably, constricting member 10 is first expanded to constrict the lumen of the right common carotid artery, causing progressive decline in the right ECA pressure. Constricting member 60, when present, is expanded to further reduce the right ECA pressure to create a favorable pressure gradient between the right ICA and the right ECA to reverse blood flow into the right ECA. Constrictor 20 may also be expanded to increase blood flow to left CCA 80 and left subclavian artery 84, thereby augmenting collateral circulation down right internal carotid artery 86. Alternatively, constrictor 20 is expanded in the aorta prior to expanding constrictor 10 in the right common carotid artery. After reversal of blood flow is verified angiographically, a therapeutic instrument, such as an atherectomy catheter, is inserted through lumen 5 to treat the occluding lesion. Embolic debris generated during the procedure is diverted from the right ICA 86 toward right ECA 79, thereby preventing distal cerebral embolization and ischemic stroke. This same technique can be used to reverse blood flow in the left ICA to the left ECA by locating occluding balloon 10 in the left CCA, constrictor 20 in the descending aorta, and optional constrictor 60 in the left ECA.

Figure 15B:
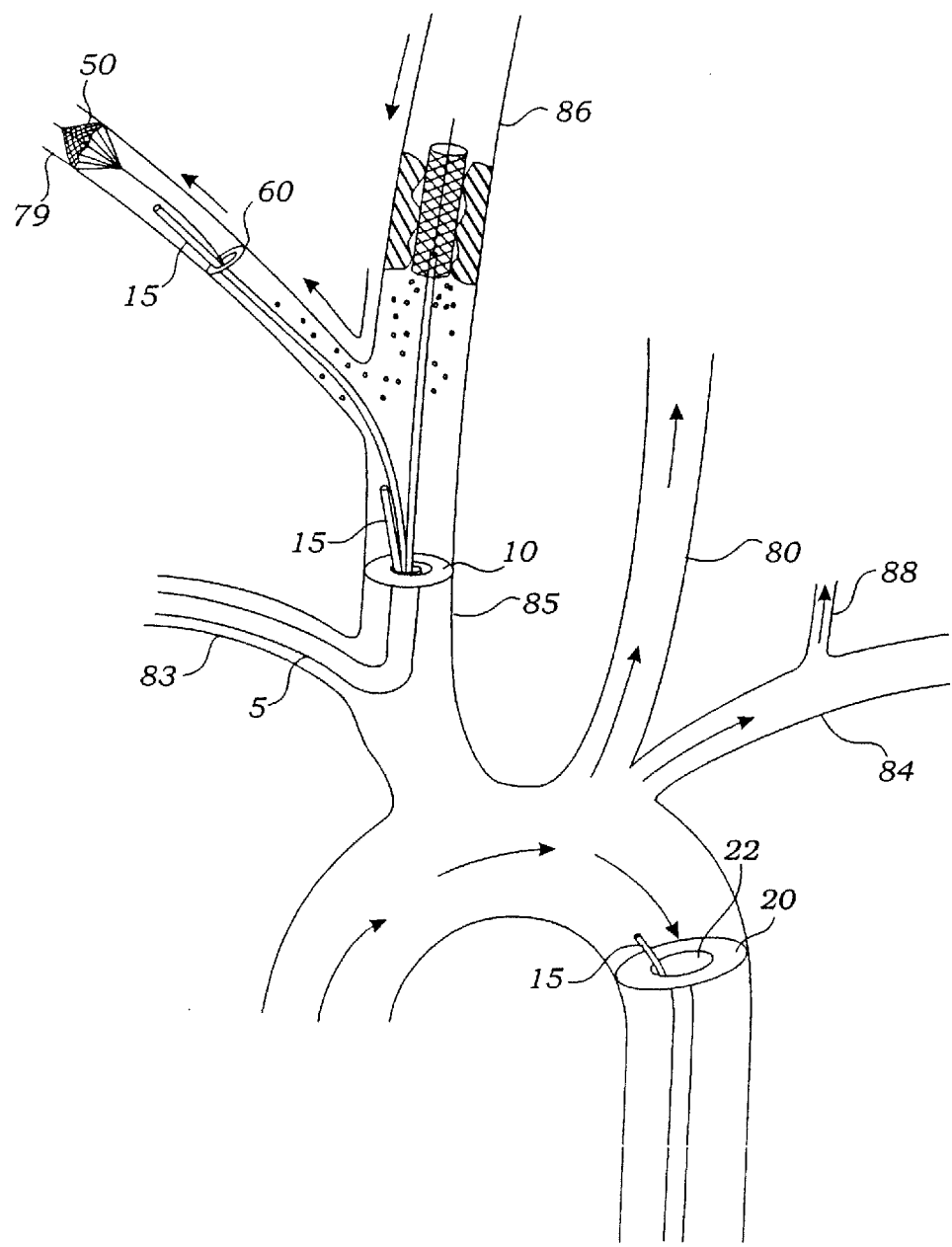
FIG. 15B depicts reversal of blood flow from the right internal carotid artery into the right external carotid artery with filter protection in the right ECA during stent treatment of an internal carotid lesion.

Alternatively, to treat an occluding lesion in the right internal carotid artery using the flow reversal from the ICA to the ECA, the device of FIG. 5C is inserted through the right subclavian artery as shown in FIG. 15B. Constricting member 60, when present, is positioned in right external carotid artery 79, and constricting member 10 is positioned in right common carotid artery 85. Filter 50 may be inserted through lumen 5 and deployed downstream of constricting member 60. A catheter carrying constricting member 20 is inserted in the descending aorta. Preferably, constricting member 10 is first expanded to constrict the lumen of the right common carotid artery, causing progressive decline in the right ECA pressure. Constricting member 60, when present, is expanded to further reduce the right ECA pressure to create a favorable pressure gradient between the right ICA and the right ECA to reverse blood flow into the right ECA. Constrictor 20 is also expanded to increase blood flow to left CCA 80 and left subclavian artery 84, thereby augmenting collateral circulation down right internal carotid artery 86. Alternatively, constrictor 20 is expanded in the aorta prior to expanding constrictor 10 in the right common carotid artery. After reversal of blood flow is verified angiographically, a therapeutic instrument, such as stent deployment catheter as shown, may be inserted through lumen 5 to treat the occluding lesion. Embolic debris generated during the procedure is diverted from the right ICA 86 toward right ECA 79 and captured by filter 50, thereby preventing distal cerebral embolization and ischemic stroke.

Figure 16:
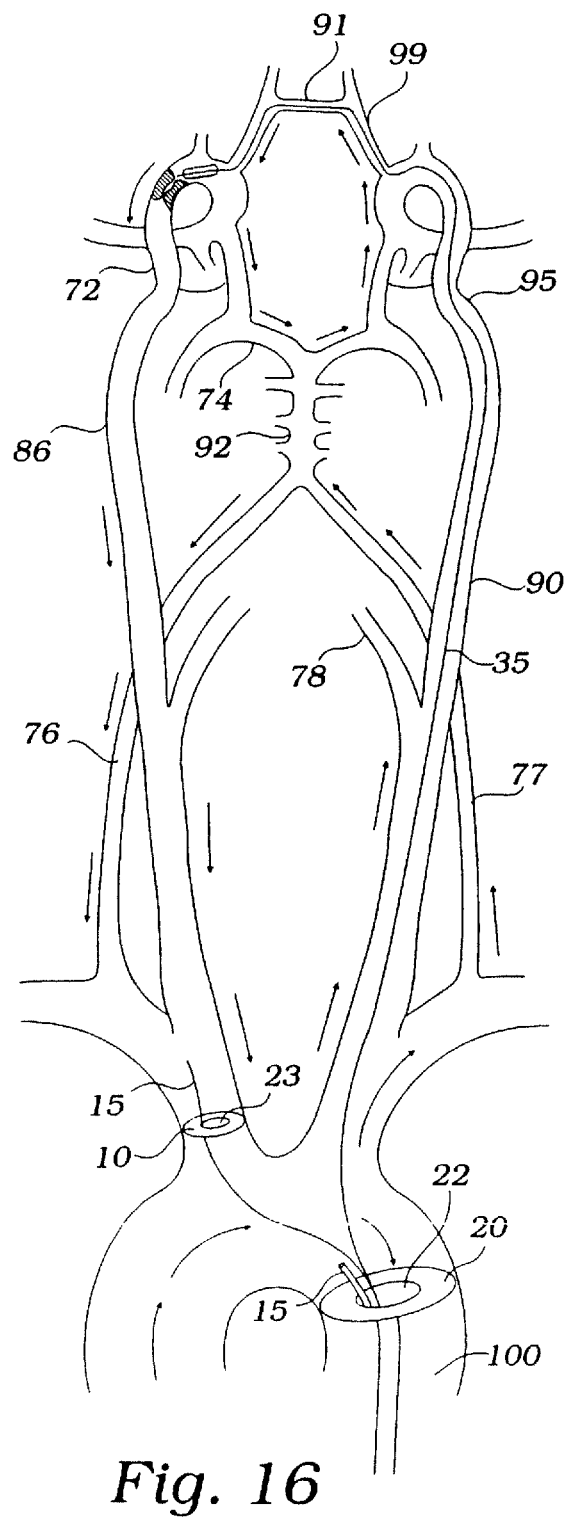
FIG. 16 depicts reversal of blood flow in the cerebral circulation during treatment of a lesion in the right carotid siphon using the device of FIG. 5C.

In treating a lesion in right carotid siphon, for example, the distal device of FIG. 5 is first inserted in the right brachiocephalic artery as shown in FIG. 16. Constrictor 10 is slowly expanded in the right brachiocephalic artery causing progressive decline in the right brachiocephalic and right CCA pressure. Constrictor 20 is then slowly expanded to constrict the descending aorta, thereby causing augmentation of collateral blood flow down the carotid siphon and right ICA 86 via the circle of Willis by increasing blood flow to the left CCA and left subclavian artery. Alternatively, constrictor 20 is expanded prior to expanding constrictor 10. After blood reversal is established, interventional catheter 35 can be inserted through the device, port 23, up the right CCA, and the right ICA (not shown) to treat the lesion in the carotid siphon. Alternatively, interventional catheter 35 can be inserted through port 22, up the left CCA, left ICA, left carotid siphon, and anterior communicating artery 91 of the circle of Willis to reach the right carotid siphon as shown. This alternative method may be desirable because it avoids crossing the lesion in the right carotid siphon, and because direct access to certain cerebral lesions, such as ateriovenous malformation, cerebral aneurysm, or highly stenotic atheroma, usually results in devastating complications, e.g., vascular rupture and/or hemorrhage.

Figure 17:
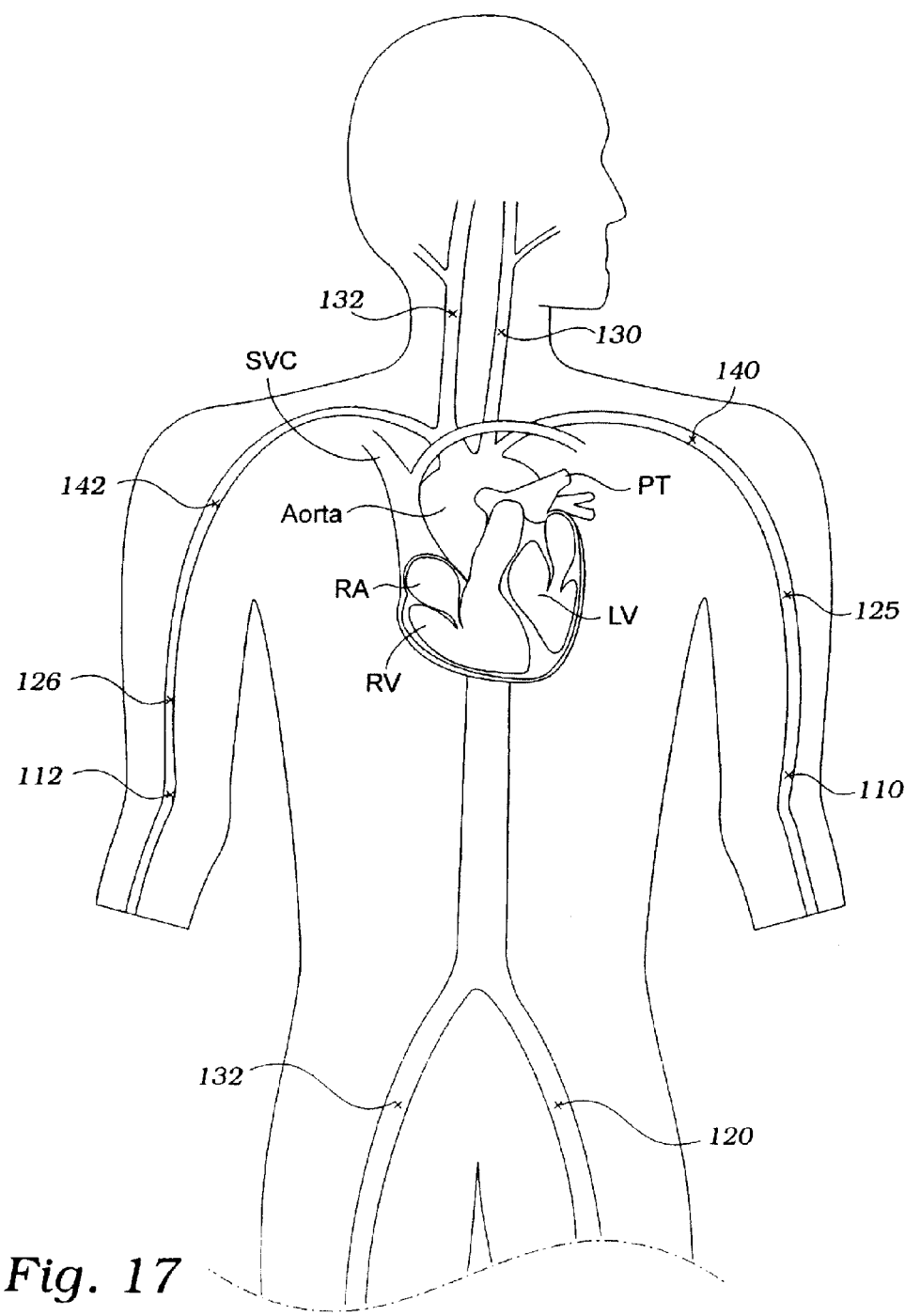
FIG. 17 depicts incision sites on various peripheral arteries for the insertion of the medical devices.
Figure 18:
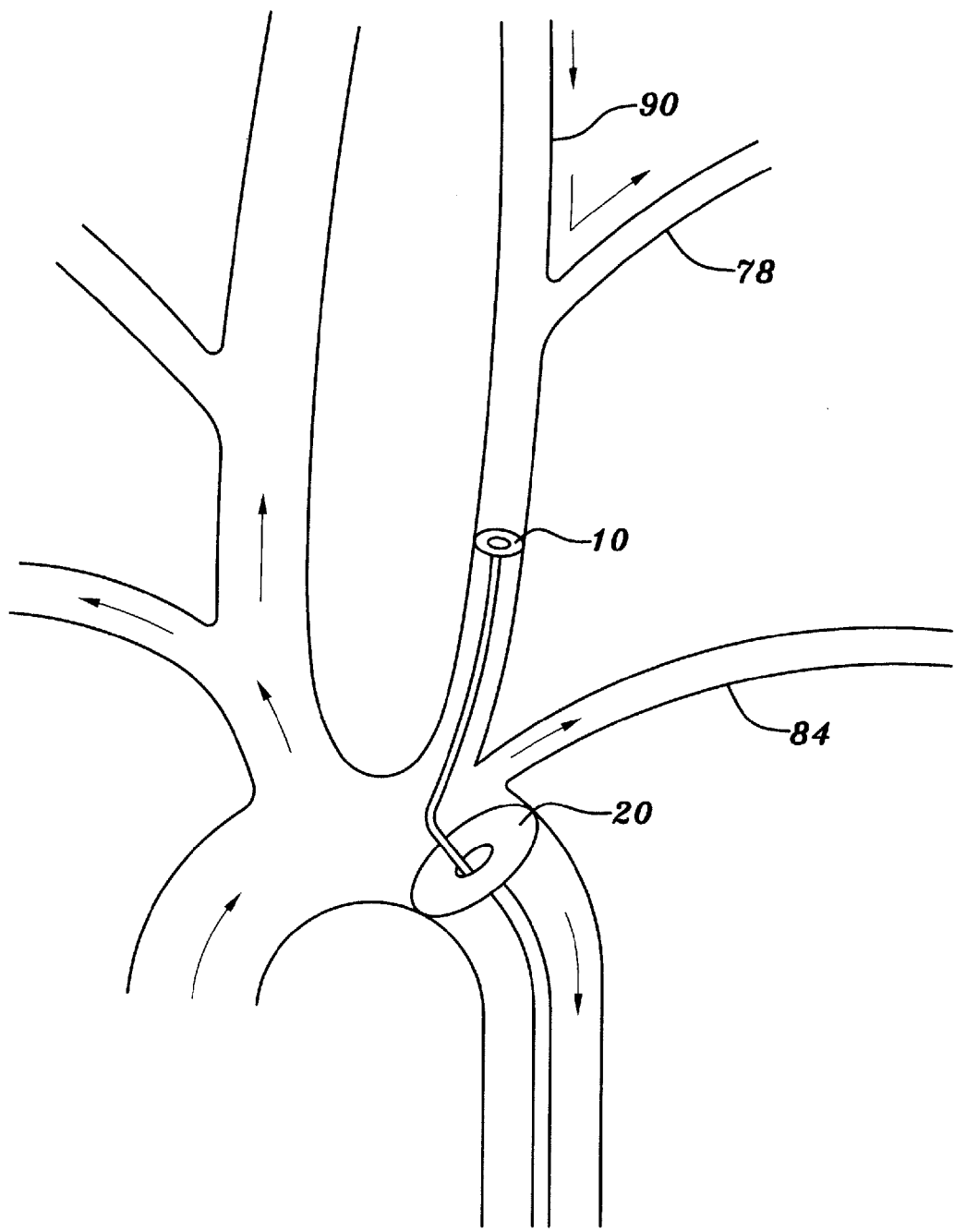
FIG. 18 depicts a constrictor positioned in the aorta downstream of the left subclavian artery and a constrictor positioned in the left common carotid artery to reverse blood flow in the internal carotid artery.

FIG. 17 depicts different sites of entry for the devices disclosed herein. An incision can be made on any peripheral artery, such as right femoral artery 132, left femoral artery 120, right brachial artery 112, left brachial artery 110, right axillary artery 126, left axillary artery 125, right subclavian artery 142, or left subclavian artery 140.

The length of catheter will generally be between 10 and 200 centimeters, preferably approximately between 30 and 150 centimeters. The inner diameter of the catheter lumen will generally be between 0.2 and 0.8 centimeters, preferably approximately between 0.3 and 0.5 centimeters. The diameter of the expanded occluder will generally be between 0.3 and 2 centimeters, preferably approximately 0.5 and 1.0 centimeters. The diameter of the expanded aortic constrictor will generally be between 0.5 and 3.5 centimeters, preferably approximately 1.5 and 2.5 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, the devices, features, and methods shown in any described embodiment can be used in any other described embodiment. It will also be understood that occlusion-constrictor 10 may be used in combination with filter 50 with or without constrictor 20 in the aorta for each embodiment. Moreover, occlusion-constrictor 10 may be used in combination with constrictor 20 in the aorta with or without filter 50 for each embodiment.

What is claimed is:

1. A method for reversing blood flow in a cerebral artery, comprising the steps of:
   locating a first constricting member in the right common carotid artery;
   locating a second constricting member in the aorta downstream of the left common carotid artery;
   expanding the first constricting member to at least partially obstruct the right common carotid artery; and
   expanding the second constricting member to at least partially obstruct the aorta, wherein blood flow is reversed in the right internal carotid artery.

2. The method of claim 1, further comprising the step of deploying a filter in the right external carotid artery to capture embolic debris.

3. The method of claim 1, further comprising the steps of advancing an interventional catheter into the right internal carotid artery and performing a procedure on a lesion in the right internal carotid artery.

4. The method of claim 3, wherein the interventional instrument is an angioplasty catheter.

5. The method of claim 3, wherein the interventional instrument is an atherectomy catheter.

6. The method of claim 3, wherein the interventional instrument is a stent delivery catheter.

7. The method of claim 1, wherein the first constricting member is inserted through a subclavian artery.

8. The method of claim 1, wherein the first constricting member is inserted through a subclavian artery and the second constricting member is inserted through a femoral artery.

\* \* \* \* \*